United States Patent
Mahmoud et al.

(10) Patent No.: US 11,260,113 B1
(45) Date of Patent: Mar. 1, 2022

(54) NK-LYSIN PEPTIDE COMPOSITIONS AND METHODS FOR THEIR USE AS ANTIMICROBIAL/ANTIVIRAL AGENTS

(71) Applicant: King Abdulaziz University, Jeddah (SA)

(72) Inventors: Maged Mostafa Mahmoud, Jeddah (SA); Haitham A. Yacoub, Jeddah (SA); Ahmed M. Al-Hejin, Jeddah (SA); Turki Abujaml, Jeddah (SA); Sherif Abd-Elmaksoud, Jeddah (SA)

(73) Assignee: King Abdulaziz University, Jeddah (SA)

(*) Notice: Subject to any disclaimer, the term of this patent is extended or adjusted under 35 U.S.C. 154(b) by 0 days.

(21) Appl. No.: 17/213,483

(22) Filed: Mar. 26, 2021

(51) Int. Cl.
| | |
|---|---|
| *A61K 38/47* | (2006.01) |
| *A61K 38/20* | (2006.01) |
| *A61P 31/14* | (2006.01) |
| *A61K 45/06* | (2006.01) |
| *A61P 31/04* | (2006.01) |
| *A61K 33/38* | (2006.01) |

(52) U.S. Cl.
CPC .............. *A61K 38/47* (2013.01); *A61K 33/38* (2013.01); *A61K 38/2013* (2013.01); *A61K 45/06* (2013.01); *A61P 31/04* (2018.01); *A61P 31/14* (2018.01); *C12Y 302/01017* (2013.01)

(58) Field of Classification Search
CPC .................................................... A61K 38/47
See application file for complete search history.

(56) References Cited

U.S. PATENT DOCUMENTS

| | | |
|---|---|---|
| 8,703,134 B2 | 4/2014 | Imboden et al. |
| 2008/0269122 A1 | 10/2008 | Imboden et al. |
| 2016/0317647 A1 | 11/2016 | Ciaramella et al. |

OTHER PUBLICATIONS

Chen: "Bovine NK-Lysins: Genomic Expansion and Fuctional Diversification", A Dissertation, May 2016.
Gelhaus et al: "The Antimicrobial Peptide NK-2, the Core Region of Mammalian NK-Lysin, Kills Intraerythrocytic Plasmodium falciparum", Antimicrobial Agnets and Chemotherapy, vol. 52, No. 5, pp. 1713-1720 May 2008.
Jacobs et al: "NK-Lysin and Its Shortened Analog NK-2 Exhibit Potent Activities against Trypanosoma cruzi", Antimicrobial Agents and Chemotherapy, vol. 47, No. 2, pp. 607-613, Feb. 2003.
Levy: "Antimicrobial proteins and peptides: anti-infective molecules of mammalian leukocytes", Journal of Leukocyte Biology, vol. 76, pp. 909-925, Nov. 2004.
Tooke et al: "[beta]-Lactamases and [beta]-Lactamase Inhibitors in the 21st Century", Journal of Molecular Biology, vol. 431, No. 18, pp. 3472-3500, Aug. 23, 2019.

*Primary Examiner* — Prema M Mertz
(74) *Attorney, Agent, or Firm* — WC&F IP

(57) ABSTRACT

Natural killer (NK)-lysin peptides from chicken, bovine and human species are used as an antimicrobial or antiviral agent alone or in combination with other agents. A pharmaceutical composition comprising NK-lysin peptides was effective against Rotavirus and various gram-negative and gram-positive bacteria that were tested. Combinations of NK-lysin peptides plus silver nanoparticles or IL-2 were also effective against *Salmonella typhimurium*. Treatment with the NK-lysin peptides repressed β-lactam-resistance genes (CTX-M-1, CTX-M-8 and CTX-M-9) in bacterial species tested and thus can be used to augment treatment with β-lactams and increase bacterial sensitivity to this important class of antibiotics.

1 Claim, 21 Drawing Sheets

Specification includes a Sequence Listing.

cNk-lysin bNk-lysin hNk-lysin

Bacterial control

```
                        SEQUENCE LISTING

<160> NUMBER OF SEQ ID NOS: 25

<210> SEQ ID NO 1
<211> LENGTH: 30
<212> TYPE: PRT
<213> ORGANISM: Artificial Sequence
<220> FEATURE:
<223> OTHER INFORMATION: Chicken NK-lysin peptide

<400> SEQUENCE: 1

Pro Asp Glu Asp Ala Ile Asn Asn Ala Leu Asn Lys Val Cys Ser Thr
1               5                   10                  15

Gly Arg Arg Gln Arg Ser Ile Cys Lys Gln Leu Leu Lys Lys
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: bovine NK-lysin peptide

<400> SEQUENCE: 2

Arg Pro Ser Lys Asn Val Ile Ile His Val Thr Ser Asn Val Cys Ser
1               5                   10                  15

Lys Met Gly Leu Trp Ser Ile Leu Cys Asn Gln Met Met Lys
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Human NK-lysin peptide

<400> SEQUENCE: 3

Pro Thr Gln Arg Ser Val Ser Asn Ala Ala Thr Arg Val Cys Arg Thr
1               5                   10                  15

Gly Arg Ser Arg Trp Arg Asp Val Cys Arg Asn Phe Met Arg
            20                  25                  30

<210> SEQ ID NO 4
<211> LENGTH: 17
<212> TYPE: DNA
<213> ORGANISM: Artificial Sequence
<220> FEATURE:
<223> OTHER INFORMATION: Salmonella typhimurium forward primer

<400> SEQUENCE: 4
cctacgggag gcagcag                                                  17

<210> SEQ ID NO 5
<211> LENGTH: 18
<212> TYPE: DNA
```

```
<213> ORGANISM: Artificial Sequence
<220> FEATURE:
<223> OTHER INFORMATION: Salmonella typhimurium reverse primer

<400> SEQUENCE: 5
attaccgcgg ctgctggc                                                  18

<210> SEQ ID NO 6
<211> LENGTH: 20
<212> TYPE: DNA
<213> ORGANISM: Artificial Sequence
<220> FEATURE:
<223> OTHER INFORMATION: BLATem forward primer

<400> SEQUENCE: 6
atgagtattc aacatttccg                                                20

<210> SEQ ID NO 7
<211> LENGTH: 22
<212> TYPE: DNA
<213> ORGANISM: Artificial Sequence
<220> FEATURE:
<223> OTHER INFORMATION: BLATem reverse primer

<400> SEQUENCE: 7
gacagttacc aatgcttaat ca                                             22

<210> SEQ ID NO 8
<211> LENGTH: 20
<212> TYPE: DNA
<213> ORGANISM: Artificial Sequence
<220> FEATURE:
<223> OTHER INFORMATION: CTX-M1 forward primer

<400> SEQUENCE: 8
gacgatgtca ctggctgagc                                                20

<210> SEQ ID NO 9
<211> LENGTH: 19
<212> TYPE: DNA
<213> ORGANISM: Artificial Sequence
<220> FEATURE:
<223> OTHER INFORMATION: CTX-M1 reverse primer

<400> SEQUENCE: 9
agccgccgac gctaataca                                                 19

<210> SEQ ID NO 10
<211> LENGTH: 22
<212> TYPE: DNA
<213> ORGANISM: Artificial Sequence
<220> FEATURE:
<223> OTHER INFORMATION: TOHO1 forward primer

<400> SEQUENCE: 10
gcgacctggt taactacaat cc                                             22

<210> SEQ ID NO 11
<211> LENGTH: 21
<212> TYPE: DNA
<213> ORGANISM: Artificial Sequence
<220> FEATURE:
<223> OTHER INFORMATION: TOHO1 reverse primer

<400> SEQUENCE: 11
cggtagtatt gcccttaagc c                                              21
```

<210> SEQ ID NO 12
<211> LENGTH: 21
<212> TYPE: DNA
<213> ORGANISM: Artificial Sequence
<220> FEATURE:
<223> OTHER INFORMATION: CTX-M8 forward primer

<400> SEQUENCE: 12
cgctttgcca tgtgcagcac c                                    21

<210> SEQ ID NO 13
<211> LENGTH: 18
<212> TYPE: DNA
<213> ORGANISM: Artificial Sequence
<220> FEATURE:
<223> OTHER INFORMATION: CTX-M8 reverse primer

<400> SEQUENCE: 13
gctcagtacg atcgagcc                                        18

<210> SEQ ID NO 14
<211> LENGTH: 20
<212> TYPE: DNA
<213> ORGANISM: Artificial Sequence
<220> FEATURE:
<223> OTHER INFORMATION: CTXM9 forward primer

<400> SEQUENCE: 14
gctggagaaa agcagcggag                                      20

<210> SEQ ID NO 15
<211> LENGTH: 20
<212> TYPE: DNA
<213> ORGANISM: Artificial Sequence
<220> FEATURE:
<223> OTHER INFORMATION: CTXM9 reverse primer

<400> SEQUENCE: 15
gtaagctgac gcaacgtctg                                      20

<210> SEQ ID NO 16
<211> LENGTH: 21
<212> TYPE: DNA
<213> ORGANISM: Artificial Sequence
<220> FEATURE:
<223> OTHER INFORMATION: gyrase A forward primer

<400> SEQUENCE: 16
aaatctgccc gtgtcgttgg t                                    21

<210> SEQ ID NO 17
<211> LENGTH: 20
<212> TYPE: DNA
<213> ORGANISM: Artificial Sequence
<220> FEATURE:
<223> OTHER INFORMATION: gyrase A reverse primer

<400> SEQUENCE: 17
gccataccta ctgcgatacc                                      20

<210> SEQ ID NO 18
<211> LENGTH: 20
<212> TYPE: DNA
<213> ORGANISM: Artificial Sequence
<220> FEATURE:

```
<223> OTHER INFORMATION: QnrA forward primer

<400> SEQUENCE: 18
atttctcacg ccaggatttg                                           20

<210> SEQ ID NO 19
<211> LENGTH: 20
<212> TYPE: DNA
<213> ORGANISM: Artificial Sequence
<220> FEATURE:
<223> OTHER INFORMATION: QnrA reverse primer

<400> SEQUENCE: 19
gatcggcaaa ggttaggtca                                           20

<210> SEQ ID NO 20
<211> LENGTH: 20
<212> TYPE: DNA
<213> ORGANISM: Artificial Sequence
<220> FEATURE:
<223> OTHER INFORMATION: QnrB forward primer

<400> SEQUENCE: 20
gatcgtgaaa gccagaaagg                                           20

<210> SEQ ID NO 21
<211> LENGTH: 20
<212> TYPE: DNA
<213> ORGANISM: Artificial Sequence
<220> FEATURE:
<223> OTHER INFORMATION: QnrB reverse primer

<400> SEQUENCE: 21
acgatgcctg gtagttgtcc                                           20

<210> SEQ ID NO 22
<211> LENGTH: 22
<212> TYPE: DNA
<213> ORGANISM: Artificial Sequence
<220> FEATURE:
<223> OTHER INFORMATION: QnrD forward primer

<400> SEQUENCE: 22
cgagatcaat ttacggggaa ta                                        22

<210> SEQ ID NO 23
<211> LENGTH: 18
<212> TYPE: DNA
<213> ORGANISM: Artificial Sequence
<220> FEATURE:
<223> OTHER INFORMATION: AnrD reverse primer

<400> SEQUENCE: 23
aacaagctga agcgcctg                                             18

<210> SEQ ID NO 24
<211> LENGTH: 20
<212> TYPE: DNA
<213> ORGANISM: Artificial Sequence
<220> FEATURE:
<223> OTHER INFORMATION: QnrS forward primer

<400> SEQUENCE: 24
acgacattcg tcaactgcaa                                           20
```

```
<210> SEQ ID NO 25
<211> LENGTH: 20
<212> TYPE: DNA
<213> ORGANISM: Artificial Sequence
<220> FEATURE:
<223> OTHER INFORMATION: QnrS reverse primer

<400> SEQUENCE: 25
taaattggca ccctgtaggc                                               20
```

NK-LYSIN PEPTIDE COMPOSITIONS AND METHODS FOR THEIR USE AS ANTIMICROBIAL/ANTIVIRAL AGENTS

BACKGROUND OF THE INVENTION

Field of the Invention

The invention generally relates NK-lysin peptides as antimicrobial or antiviral agents alone or in combination with other agents, including β-lactam and/or other antibiotics, and with interleukin-2 or silver nanoparticles. The invention further relates to methods for treating microbial or viral infection with a pharmaceutical composition comprising NK-lysin peptides.

Background

Antimicrobial peptides (AMPs) are immune response molecules that have been found in various organisms. AMPs play a fundamental role in first line of defense against invading pathogens to inhibit properties that mediate fitness to cause infection. Moreover, AMPs also perform immune-modulatory functions. NK-lysin is a cationic AMP with antibacterial activity that was first identified from pig gastrointestinal tract. It was also found to be secreted from the granules of natural killer and cytotoxic T cells, and thus acquired the name of NK-lysin. NK-lysin is referred to as granulysin in humans and is a saposin-like protein family member. The peptide possesses a strong positive charge conferred by its conserved cysteines residues, which are also responsible for disulfide bonds formation inside the amino acids chain. The 3-D structural characteristics have been shown to increase its antimicrobial potentialities. The ability to move through bacterial membrane is critically due to the number of non-polar amino acids at the side chain of the NK-lysin peptide. Accordingly, these non-polar amino acids are highly conserved and account for 27-51% of the amino acid residues in NK-lysin homologues within all animal species.

Peptide binding and disruption of cell membranes is facilitated by non-polar amino acids such as Ile and Leu. NK-lysin and granulysin peptides comprise a saposin domain with minor changes in domain length. The domain is folded in 4-5 helical bundles, depending upon the species, having three disulfide bonds between six cysteine residues that stabilize the peptide conformational structure.

The topic of antibiotic resistance is dynamic, with new data and concepts shaping and reshaping the field on a continuous basis. The topics of greatest interest in this field include β-lactam antibiotic resistance and specifically β-lactamases, the enzymes that are capable of hydrolysing β-lactam antibiotics. Since the 1980s, the number of β-lactamases identified has increased significantly; however, alternative ways were taken into consideration by healthcare and pharmaceutical Industry to improve and invent new routes to combat and prevent multi-drug resistance pathogens by using biocompatible non-toxic agents. For example, uptake of silver nanoparticles has been used to prevent infection with both gram-positive and negative bacteria. Recently, silver nanoparticles combined with antimicrobial peptides and/or antibiotic have been investigated as a means to eliminate bacterial resistance and improve antimicrobial molecules.

Several biomolecule classes, including cytokines and chemokines, have exhibited antibacterial activities in addition to their immune-regulatory properties. The binding affinity between positively charged chemokines and negatively charged phospholipids in the cell membrane bilayer may underly the mode of action that causes membrane disruption. Interleukin-2 (IL-2) is an example of a cytokine that has multiple roles in defences against disease. IL-2 plays an important role in managing the immune system, and it is also used as a medication to treat different oncological diseases. A combination of interleukin and lysozyme shows highest activity in the micromolar range of antibiotics. It was recently reported that IL-2 has bacteriolytic activity, but the physiologically significant for this has not yet been demonstrated.

Various studies have demonstrated that innate immune response molecules may have antiviral effects on enveloped and non-enveloped viruses and teach that membrane disruption is a mode of action induced against viral infection. For example, Levy (*J Leuk Bio* 76:909, November 2004) teaches that lymphocytes such as NK-cells express granulysin or the non-human homologue NK-lysin and that granulysin is a membrane-active peptide with activity against a range of bacteria, including *M. tuberculosis* and that the IL-2 inducible NK-lysin and granulysin also has antimycobacterial activity. Levy teaches that KN-lysin binds LPS and has an inhibitory effect. Jacobs et al. (Antimicrob Agents Chemo 47(2):607) teach that porcine NK-lysin and a shortened analog NK-2 have antimicrobial activity against *T. cruzi*. Jacobs teaches that NK-2 is less cytotoxic to mammalian cells than NK-lysin, while retaining antimicrobial activity against bacteria, yeast and protozoa by disruption of microbial membranes. U.S. Pat. No. 8,703,134 teaches a fusion protein to target various microorganisms, comprising an immunoglobulin and a biocide comprising IL-2 or granulysin. Synthetic NK-lysin peptides, which correspond with functional region helices 2 and 3, showed similar hydrophobicity ranging from 40 to 43% and net positive charge of 5.0-7.9. The peptides comprise 20-30% basic residues, which contribute to high effectiveness against *S. aureus* and *E. coli*. The high alphahelicity of the bovine peptide did not have much effect on *M. bovis* and M haemolytic isolates (Chen et al., *PLoS One;* 2016; 11(7):e0158882), but in contrast bovine NK lysin peptide was highly effective towards *H. somni* isolates (Dassanayake et al. *PLoS One.* 2017; 12(8):e0183610; and Dassanayake et al. 2018*; PLoS One* 13(5): e0197677). Studies which were done on chicken NK lysin peptide show their antimicrobial activity is similar to other NK lysin peptides (Harwig et al. *FEBS Lett.* 1994; 342:281-5; Lehrer and Ganz. *Curr Opin Immunol.* 2002; 14:96-102; Goitsuka et al *Proc Natl Acad Sci USA.* 2007; 104:15063-8; Lee et al. *Proc Natl Acad Sci USA.* 2012; 109:12087-92; and Lee et al. *Poult Sci.* 2014; 93:864-70). Research by (Jacobs et al., 2003, *PNAS* Nov. 25, 2003 100 (24) 14339-14344) shows that the mammalian NK-lysin peptide rapidly permeabilized the plasma membrane of the protozoan parasite *Trypanosoma cruzi,* resulting in the release of cytosolic enzymes within minutes after exposure. They also found that the NK-lysin and NK-2 killed trypanosomes residing inside the human glioblastoma cell line 86HG39 but only NK-2 left the host cells apparently unharmed, whereas NK-lysin was not safe. Pheasant cathelicidin-1 (Pc-CATH1) showed similar data, where the growth of *E. coli* was restricted after 1 hour of exposure, and even after 6 hours of being exposed the bacteria did not start growing (Wang et al., 2011*, Curr. Microbiol.* 62, 703-709. doi: 10.1007/s00284-010-9767-2). Melimine peptide and its derivative exhibit a powerful antimicrobial activity against *P. aeruginosa* because it is smaller in size (17-29 aa), which is possibly why it is capable of covering the cytoplasmic membrane of *P. aeruginosa*. The smaller length of the MeI4 peptide is thought to take more time to move across the outer membrane or to interact with the inner membrane of *P. aeruginosa* to destroy the bacteria, or that it needs to align itself inside the membrane more effectively so as to start its activity.

Levashov et al. (*Acta Naturae.* 2017; 8:1(33):81-87) demonstrated that IL-2 has a bacteriologic activity in the micromolar range, and that a combination of IL-2 and lysozyme has bacteriolytic activity in the micromolar range. The physiological significance of bacteriolytic activity for this cytokine remains unclear.

Though studies on NK-lysin peptides have been carried out in terms of their antibacterial activity against some microbial pathogens, the potential of bovine, human and chicken NK-lysin peptides as antimicrobial and/or antiviral agents, alone or in combination with other agents, has not been fully established. Furthermore, the potential for sensitizing antibiotic-resistant bacterial pathogens to beta-lactam antibiotics is an ongoing and urgent need.

SUMMARY OF THE INVENTION

NK-lysins from chicken, bovine and human are used as antiviral and antibacterial agents.

Gram-negative and gram-positive microorganisms, including *Streptococcus pyogenes, Streptococcus mutans, Escherichia coli, Pseudomonas aeruginosa, Klebsiella oxytoca, Shigella sonnei, Klebsiella pneumoniae* and *Salmonella typhimurium*, are susceptible to NK-lysin treatment. The NK-lysin peptides and compositions comprising these peptides are also effective as a treatment against Rotavirus species. Combinations of NK-lysin with IL-2 or silver nanoparticles are also effective against *S. typhimurium*. Expression of β-lactamase genes, including CTX-M-1, M-8 and M-9 is inhibited in response to treatment with NK-lysins. Bacterial resistance to β-lactam antibiotics is at least partially overcome by inhibiting β-lactamase activity. NK-lysin peptides are also used to test for inhibition of infectivity, which ranged from 50-90% depending on NK-lysin species.

In one embodiment, the invention is a method for treating an infection in a patient in need thereof, comprising the step of administering to the patient a therapeutically effective amount of a pharmaceutical composition comprising an NK-lysin peptide, wherein the infection is caused by a pathogen selected from the group consisting of *Streptococcus pyogenes, Streptococcus mutans, Escherichia coli, Pseudomonas aeruginosa, Klebsiella oxytoca, Klebsiella pneumoniae, Shigella sonnei* and *Salmonella typhimurium*. The NK-lysin peptide is derived from a chicken, bovine or human protein or peptide. The chicken NK-lysin peptide has the amino acid identity of SEQ ID NO:1, the bovine NK-lysin peptide has the amino acid identity of SEQ ID NO:2 and the human NK-lysin peptide, also known as granulysin, has the amino acid identity of SEQ ID NO:3.

In another embodiment, the invention is a method for treating a rotaviral infection in a subject in need thereof, comprising the step of administering to the patient a therapeutically effective amount of a pharmaceutical composition comprising an NK-lysin peptide, wherein the NK-lysin peptide has an amino acid identity selected from the group consisting of SEQ ID NO:1, SEQ ID NO:2 and SEQ ID NO:3. In one embodiment of the invention the antiviral agent is a bovine NK-lysin peptide having the amino acid identity of SEQ ID NO:2.

In yet another embodiment, the invention is a method of treating a bacterial infection wherein the bacterial infection is caused by a pathogen that is or is suspected to be resistant to 0-lactam antibiotics, comprising the step of co-administering at least one β-lactam antibiotic and a therapeutically effective amount of NK-lysin peptide, wherein the therapeutically effective amount of NK-lysin peptide is sufficient to inhibit expression of at least one bacterial β-lactamase gene selected from the group consisting of CTX-M-1, M-8 and M-9. The NK-lysin peptide has an amino acid identity selected from the group consisting of SEQ ID NO:1, SEQ ID NO:2 and SEQ ID NO:3.

Other features and advantages of the present invention will be set forth in the description of invention that follows, and in part will be apparent from the description or may be learned by practice of the invention. The invention will be realized and attained by the compositions and methods particularly pointed out in the written description and claims hereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

FIG. 6A shows the activity of hNK-lysin alone against *Salmonella typhimurium*. FIG. 6B shows the activity of hNK-lysin+Nanosilver against *S. typhimurium*. Data presented as means (±SD) of three independent repeats in triplicate.

FIG. 8A shows activity of human NK-lysin peptide compared to control, and FIG. 8B shows activity of human IL-2 (+hNK-lysin+human IL-2) compared to control. Data presented as means (±SD) of three independent repeats in triplicate.

FIG. 12A shows chicken NK-lysin peptides, FIG. 12B shows bovine NK-lysin peptides, and FIG. 12C shows human NK-lysin peptides. Bacterial control without NK-lysin treatment is shown in FIG. 12D. Green fluorescence indicates the presence of live bacteria.

DETAILED DESCRIPTION

Figure 1A:
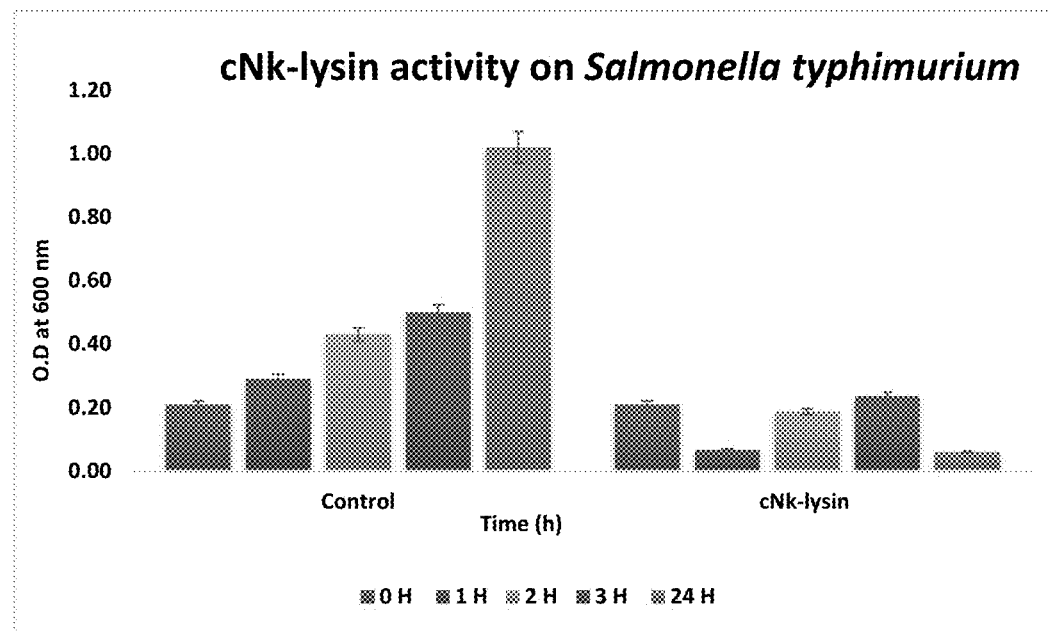
FIGS. 1A-1C shows antimicrobial activity of NK-lysin peptides of 1A) chicken, 1B) bovine and 1C) human against *Salmonella typhimurium*. Data presented as means (±SD) of three independent repeats in triplicate.

The following descriptions and examples illustrate some exemplary embodiments of the disclosed invention in detail. Those of the skill in the art will recognize that there are numerous variations and modifications of this invention that are encompassed by its scope. Accordingly, the description of a certain exemplary embodiment should not be deemed to limit the scope of the present invention.

NK-lysins from chicken, bovine and human are used as antiviral and antibacterial agents. Gram-negative and gram-positive microorganisms, including *Streptococcus pyogenes, Streptococcus mutans, Escherichia coli, Pseudomonas aeruginosa, Klebsiella oxytoca, Shigella sonnei, Klebsiella Pneumonia*, and *Salmonella typhimurium*, are susceptible to NK-lysin treatment. The NK-lysin peptides and compositions comprising these peptides are also effective as a treatment against Rotavirus species. Combinations of NK-lysin with IL2 (NK-lysin+IL-2) or silver nanoparticles (NK-lysin+AgNP) are also effective against *Salmonella typhimurium*. Expression of β-lactamase genes, including CTX-M-1, M-8 and M-9 is inhibited in response to treatment with NK-lysins. Bacterial resistance to β-lactam antibiotics is at least partially overcome by inhibiting β-lactamase expression or activity. NK-lysin peptides are also used to test for inhibition of infectivity, which ranged from 50-90% depending on NK-lysin species.

In one embodiment, the invention is a method for treating an infection in a patient in need thereof, comprising the step of administering to the patient a therapeutically effective amount of a pharmaceutical composition comprising an NK-lysin peptide, wherein the infection is caused by a pathogen selected from the group consisting of *Streptococcus pyogenes, Streptococcus mutans, Escherichia coli, Pseudomonas aeruginosa, Klebsiella oxytoca, Klebsiella pneumoniae, Shigella sonnei* and *Salmonella typhimurium*. The NK-lysin peptide is derived from a chicken, bovine or human protein or peptide. The chicken NK-lysin peptide has the amino acid identity of SEQ ID NO:1, the bovine NK-lysin peptide has the amino acid identity of SEQ ID NO:2 and the human NK-lysin peptide, also known as granulysin, has the amino acid identity of SEQ ID NO:3.

In another embodiment, the invention is a method for treating a rotaviral infection in a subject in need thereof, comprising the step of administering to the patient a therapeutically effective amount of a pharmaceutical composition comprising an NK-lysin peptide, wherein the NK-lysin peptide has an amino acid identity selected from the group consisting of SEQ ID NO:1, SEQ ID NO:2 and SEQ ID NO:3. In one embodiment of the invention the antiviral agent is a bovine NK-lysin peptide having the amino acid identity of SEQ ID NO:2.

In yet another embodiment, the invention is a method of treating a bacterial infection wherein the bacterial infection is caused by a pathogen that is or is suspected to be resistant to 0-lactam antibiotics, comprising the step of co-administering at least one β-lactam antibiotic and a therapeutically effective amount of NK-lysin peptide, wherein the therapeutically effective amount of NK-lysin peptide is sufficient to inhibit expression of at least one bacterial β-lactamase gene selected from the group consisting of CTX-M-1, M-8 and M-9. The NK-lysin peptide has an amino acid identity selected from the group consisting of SEQ ID NO:1, SEQ ID NO:2 and SEQ ID NO:3.

Thus, the invention is method of delivering to a subject in need thereof a pharmaceutical composition having antibacterial activity, comprising one or more NK-lysin peptides from human, chicken, and bovine species. The pharmaceutical composition is effective against gram-negative and gram-positive bacterial infections, and further has antiviral activity against rotavirus and rotaviral infection. A pharmaceutical composition comprising NK-lysin peptides and silver nanoparticles (AgNPs) has increased antimicrobial activity, as does a pharmaceutical combination of NK-lysin peptides and interleukin-2 (IL-2). The results of treatments with the compositions of the invention showed high inhibition of bacterial activity within the first hour of treatment. Chicken NK-lysin peptides were more efficient against some bacterial strains compared to others in vitro, with killing nearly complete within 3 hours. Treatment of *Salmonella typhimurium* with 2×MIC of NK-lysin peptides demonstrated that a bacteriolytic effect was mediated by damage to the cell membrane. Treatment with NK-lysin peptides downregulated expression of β-lactamase genes known as CTX-M-1, CTX-M-8, and CTX-M-9 while all three genes were detected in untreated bacteria. Though the studies on NK-lysin peptides have been carried out in terms of their antibacterial activity. Nonetheless, no study has been carried out in the past that characterized the antiviral activity of bovine, human and chicken NK-lysin peptides. Hence, this is the foremost study on the enhanced antimicrobial activity of human, bovine and chicken NK-lysin peptides against Rotavirus (strain SA-11). The findings of the study demonstrated that the powerful antiviral activities were exhibited by NK-lysin peptides against Rotavirus (strain SA-11). In one embodiment, the invention is a pharmaceutical composition for treatment of rotaviral infection. In particular, the bovine NK-lysin peptides were potently antiviral against Rotavirus (strain SA-11), restraining infectivity by up to 90%, while infectivity was restricted by 80% by chicken NK-lysin peptides and by 50% by human NK-lysin peptides.

Details regarding the antimicrobial activity and mechanism of action of NK-lysin peptides are described in the Examples that follow. The results showed high inhibition of bacterial activity after exposure to the NK lysin peptide, especially at the first hour where the inhibition rate was 95%, this held true especially for *Salmonella typhimurium*. The results show strong activity of NK lysin peptide in all gram-negative and gram-positive bacteria tested. NK-lysin peptides had more antibacterial efficacy than kanamycin when used as a reference antibiotic. However, all NK-lysin peptides MIC values were found to be 15 μg/ml for all bacterial strains that were tested. The MIC values of kanamycin was ranged from 7.8-62.5 μg/ml. The kanamycin was effective at concentration of 62.5 μg/ml for *Salmonella typhimurium*, *Streptococcus pyogenes*, *Streptococcus mutans*, and *Pseudomonas aeruginosa*, while in the case of *Klebsiella pneumonia* and *Klebsiella oxytoca* a concentration of 31.25 μg/ml was sufficient. The MIC for *Shigella sonnei* was identified as 7.8 μg/ml of kanamycin.

A kinetic analysis of the three NK-lysin peptides showed that chicken and bovine NK-lysin peptides had a similar level of activity against *Salmonella typhimurium* with high lethality at 1 hr after treatment. The human NK-lysin peptides were not as effective, with a reduction of *Salmonella typhimurium* growth at approximately 75% after 4 hours. Chicken NK-lysin peptides were remarkably more efficient, and other bacteria being tested did not survive for even 3 hours following exposure. Without being bound by theoretical concepts, the changes in kinetics that characterize the antibacterial function of the peptide may be due hydrophilic regions and positively charged amino acids that are mainly present on the surface area of these peptides. This may regulate the mode of action of majority of the NK-lysin peptides. The results are in agreement with previous studies that had found intramolecular structures of NK-lysin to be connected through six cysteine residues creating bridge to link helical 1/helical 4/helical 5 units and helical 2/helical 3 units. The helical peptide includes a Trp residue that provides greater affinity and this has been shown to contribute to a more extensive insertion inside bacterial membranes (Torcato et al., 2013 *Biochem Biophys Acta* 1828, 944-955).

A critical part is played by the number of non-polar amino acids at the side chain of NK-lysin peptides in moving through the bacterial membrane, as these peptides consist of 27-51% of non-polar amino acids within all animal species. Peptide binding and disruption of cell membranes are known to be facilitated by non-polar amino acids, including Ile and Leu. NK-lysin peptides are part of the saposin family with minor changes in domain length. The domain is folded into 4-5 helical bundles according to species, having three disulphide bonds between six cysteine residues that stabilize the peptide conformational structure. These findings are consistent with earlier studies that showed that there were five helical folded structures in a single globular chain in the peptide and stable disulphide bridges between six cys residues in porcine NK-lysin peptide, while the human NK-lysin domain comprises four cysteine residues creating two disulphide bonds. The small size (30 amino acids) of the NK-lysin peptides and structure may also contribute to its potent activity, since studies of other antimicrobial peptides have suggested that an optimal amino acid length should be around 15-20 residues for the peptides to cover bacterial cytoplasmic membranes effectively.

Strategies to overcome microbial resistance can be based on synergistic combinations of antimicrobial agents or drug designs that employ nanotechnology and phytomedicine. Various studies have been carried out in the past few years that show that AgNPs may increase the antibacterial activities of antibiotics against susceptible as well as resistant bacteria, either in an additive manner or synergistically. There has been widespread use of AgNPs in the field of medicine since these are known to have antimicrobial properties.

The invention provides increased antimicrobial activity in the combinations of NK-lysin with AgNPs or with IL-2. These combinations can be directed against *Salmonella typhimurium* and other bacterial strains in various embodiments of the invention. AgNPs exhibited antibacterial effects and additive activity when mixed with NK-lysin peptides. Antimicrobial activity of AgNPs has a complicated mechanism and is dependent on nanoparticles as well as silver ions released from the surface of the nanoparticles. In addition, the nanoparticles interact with various cellular components (Dakal et al., 2016; *Front. Microbiol.* 7:1831). Embodiments of the invention demonstrated equal potentiality for preventing the growth of *Salmonella typhimurium*, however, when added together, there was minor increase in the level of action. The conclusion was that these combined molecules had an overlapping and slight additive effect. The combination of NK-lysin peptides and IL-2 acted synergistically. An important role is performed by interleukin-2 in managing the immune system and it is also used as a medication to treat different oncological diseases.

A concentration-dependent release of DNA/RNA (260 nm absorbing material) was brought about by the three distinct NK-lysin peptides within 15 minutes of incubation. Treatment with enterocin CRL35, melimine and its derivative Mel4 induce a concentration-dependent release of DNA/RNA from *Listeria monocytogenes* and *Pseudomonas aeruginosa*. No significant variation was noted between chicken, bovine or human NK-lysin peptides in the release of DNA/RNA after 90 minutes of exposure to the NK-lysin peptides.

The conformational structure of NK-lysin and granulysin peptides are homologous and therefore appear to act via the same pathway leading to bacterial inactivation, which is mediated through the physical interactions between the positively charged peptides and negatively charged cell membrane bilayer phospholipids, thus causing membrane disruption. Without being bound by theory regarding this mode of action, DNA/RNA is released because of the bursting and disintegration of nucleic acid, which may happen during bacterial apoptosis-like death that is identical to eukaryotic cells that brought about physiological and biothermal variations following exposure of peptides. NK-2 also disintegrated parasitic membranes to release a cytosolic marker protein, and this suggests that both mammalian NK-lysin and NK-2 target the plasma membrane of the parasite.

In one embodiment of the invention, the additive activity of IL-2 and NK-lysin peptides provides a major improvement in bactericidal activity irrespective of antibiotic resistance and is part of a multi-target antimicrobial effect also. In addition, AgNPs are effective as a combination therapeutic agent for treating infectious diseases caused by bacteria.

The presence of β-lactamase genes and plasmid-mediated quinolone-resistance genes in antibiotic-resistant bacteria is a growing problem. The topic of antibiotic resistance is continuously studied and published each year with new data that can change the way we think about this issue. The topics that have been studied most often in this field include β-lactam resistance and specifically β-lactamases, the enzymes that are capable of hydrolysing β-lactam antibiotics. Since the 1980s, the number of β-lactamases has increased significantly; however, this increase is almost entirely because of class A and D β-lactamases. From the class A β-lactamases, extended-spectrum β-lactamases (ESBLs) able to hydrolyse expanded spectrum cephalosporins (for example cefotaxime, ceftriaxone, ceftazidime, or cefepime) and monobactams (aztreonam) are cause of a major public health concern.

Antibiotics have various mechanisms against different bacterial strains that can contribute to an additive or a synergistic effect. β-lactam antibiotics that are sensitive to bacterial β-lactamases can be combined with any of the NK-lysin peptides using the methods of the invention to inhibit growth and infection caused by resistant bacterial strains. These are well-known to one of skill in the art and include but are not limited to clavulanic acid, tazobactam, sulbactam, avibactam, cloxacillin, dicloxacillin, flucloxacillin, methicillin, nafcillin, oxacillin, temocillin, but can also include penams, cephems, amoxicillin, ampicillin, carbenicillin, pipercillin, ticarcillin, azlocillin, mezlocillin cephalosporin cephamycin, carbapenems, penems, monobactams, benzathine, benzylpenicillin (Penicillin G), benzathine penicillin G, benzathine penicillin V, phenoxymethylpenicillin (penicillin V), procaine penicillin, pheneticillin, and derivatives of these.

Class A ESBLs are sensitive to β-lactamase enzyme families that include those of the TEM, CTX-M, SHV, GES and VEB enzymes. The greatest number of variants defined in the previous years are part of the CTX-M family. The Examples of the invention will show that the presence of dominant TEM-1 gene was noted in all untreated and treated bacteria, while TOHO-1 gene was absent in all bacteria. Importantly, β-lactamase genes CTX-M-1, CTX-M-8, and CTX-M-9 genes were detected in untreated bacterial strains; however, none of these were found in any bacterial strains after treatment with NK-lysin peptides. Thus, embodiments of the invention provide a novel treatment using NK-lysin peptides to inhibit expression of β-lactamase genes in β-lactam antibiotic-resistant bacterial infections.

As used herein, the term "antibiotic resistance" refers to a change that occurs in bacteria in response to the use of antibiotics or classes of antibiotics. It is generally understood that antibiotic resistance arises when a bacterium acquires an antibiotic resistance gene carried on a plasmid or extrachromosomal DNA. Retention of the plasmid is promoted by the selection pressure of an antibiotic treatment, and the acquired antibiotic resistance allows expansion of the resistant strain. However, when resistant strains are treated with the compositions of the invention, i.e., NK-lysin peptides, expression is suppressed and the plasmid carrying the resistance gene is lost since they are no longer confers a benefit to the bacteria. In other words, the methods and treatments comprising NK-lysin peptides provide a way to overcome expression of one or more antibiotic resistance genes, which leads to loss of one or more plasmid carrying the gene(s). Without being bound by theory, the sensitivity to β-lactam antibiotics observed following treatment with compositions comprising NK-lysin peptides may be driven by repression of antibiotic resistance gene expression followed by loss of antibiotic resistance gene-carrying plasmid or other extrachromosomal DNA.

The relatively slow movement in the antibiotic discovery pipeline is a concern for all who are engaged in the search for agents that are effective against gram-negative bacteria. Heretofore, various combinations of susceptible β-lactams with mechanism-based β-lactamase inhibitors represent the major strategy for combatting β-lactamase-mediated resistance. These treatments that may lead to genetic re-organization of β-lactamases enzymes during cell replication, which may cause a change in its location or integration of transposon elements. These enzymes are differentiated based on β-lactamase genes (bla) location in plasmids or chromosomes, although this classification feature is no longer reliable since it is possible to mobilize and integrate chromosomal bla genes into plasmids or transposons; however, a reverse case of initially described plasmid-mediated β-lactamases into the chromosome are known. Protein regulation features (constitutive or inducible expression) are also noted with respect to various β-lactamases groups; however, this regulation can be dependent on adjacent genes.

NK-lysin treatment may also lead to genetic re-organization of β-lactamases enzymes during cell replication, which may cause a change in its location or integration of transposon elements. Bla genes may be absent in certain isolates with decreased susceptibility tested possibly because of weak sensitivity of phenotypic resistance detection approaches and/or lack of or downregulation of features such as outer membrane porins, changes in the beta-lactam targets, varied ampC β-lactamases and overexpression of efflux to decrease susceptibility. There are certain genetic elements and plasmids with $^{bla}$CTX-M genes that also include other resistance genes, such as those encoding ampC β-lactamases (plasmid blaAmpC) and carbapenemases, methylases affecting aminoglycosides or plasmid-mediated quinolone resistance genes. These genes may also benefit $^{bla}$CTX-M for maintenance because of co-selection procedures, therefore, causing loss of fewer CTX-M genes during the process of cell division. Regulatory elements such as IS located upstream, like ISEcp1, have demonstrated the experimental mobilization of blaCTX-Ms genes. There are various IS that have been recognized upstream of the blaCTX-Ms genes, such as ISEcp1, IS10, ISCR1 and IS26. Though there are other IS elements that have also been identified upstream, they were because of ensuing integration activities. For example, IS1 and IS10 and also IS26 and ISCR1 have been found to disrupt ISEcp1. Spacer sequences between ISEcp1 and blaCTX-M genes are postulated as being linked to cephalosporin MIC values and may be an outcome of a single transposition incident.

Chicken, bovine and human NK-lysin peptides are demonstrated herein to have antibacterial activity and antiviral activity against Rotavirus (strain SA-11). On the basis of the comparison between these peptides, potent antiviral activity of bovine NK-lysin against Rotavirus (strain SA-11) is particularly evident, inhibiting infection by up to 90%.

However, growth was also significantly inhibited by chicken and human NK-lysin peptides, restricted by 80% and 50%, respectively.

It was found in various studies that there are antiviral effects of innate immune response molecules on enveloped and non-enveloped viruses and without being bound by theory, it is assumed that membrane disruption is one of the antiviral methods exhibited by defensins against enveloped viruses. A recent study by Falco et al. (Drugs 2019 (17):87) reported that powerful antiviral activity was shown by NK-lysin short peptide of the turbot (Scophthalmus maximus) against spring viremia of carp virus (SVCV) not just by restricting viral particles from binding to host cells, but also by preventing the integration of virus and cell membranes that need a low pH. Other antiviral mechanisms of these peptides appear to depend on specific binding to particular viral proteins or the non-specific lectin-like binding to the envelope glycoproteins of viruses. Taking into account this mechanism, there is also evidence that defensins may exhibit inhibitory effects by blocking the fundamental interaction between influenza glycoprotein hemagglutinin and cellular receptor sialic acid.

Some effects of the NK-lysin peptides are due to plasmid curing, as well as downregulation of β-lactamase gene expression. Plasmid curing is the elimination of a plasmid from bacteria in a cell culture, which can be achieved with a treatment at a concentration that does not inhibit chromosomal replication while remaining sufficient to inhibit plasmid replication. A plasmid-cured derivative is often sought with certain plasmid-containing bacteria so that a direct comparison can be performed between the two. There are certain plasmids that go through spontaneous segregation and deletion. But most of plasmids are quite stable and need curing agents or other conditions, such as increased growth temperature or thymine starvation to enhance the frequency of spontaneous segregation so that majority of the plasmids can enter the bacterial host chromosome. When this happens, the plasmid would no longer be present as a covalently closed circular molecule. Plasmid-mediated quinolone-resistance genes were not detected in any of the bacterial strains that were untreated or treated with NK-lysin peptides.

The NK-lysin peptides of the invention may be produced by any suitable method, many of which are known to those of skill in the art. For example, they may be chemically synthesized, or produced using recombinant DNA technology (e.g., in bacterial cells, in cell culture (mammalian, yeast or insect cells), in plants or plant cells, or by cell-free prokaryotic or eukaryotic-based expression systems, by other in vitro systems, etc.). In some embodiments, they are peptides produced using chemical synthesis methods.

The pharmaceutical composition of the invention may include one or more isolated and substantially purified type of NK-lysin peptides as described herein, and a pharmacologically suitable carrier. The peptides in the composition may be the same or different, i.e., the composition may be a "cocktail" of different peptides. The preparation of such compositions is well known to those of skill in the art. Typically, such compositions are prepared either as liquid solutions or suspensions, however solid forms such as tablets, pills, powder and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of NK-lysin peptide in the formulations may vary. However, in general, the amount in the formulations will be from about 0.01-99%, weight/volume.

The methods involve administering a composition comprising NK-lysin peptides in a pharmacologically acceptable carrier to a mammal. The mammal may be a human, but this need not always be the case, as veterinary applications of this technology are also contemplated. The preparations of the present invention may be administered by any of the many suitable means which are well known to those of skill in the art, including but not limited to by injection, inhalation, orally, intranasally, by ingestion of a food product containing the NK-lysin peptides, etc. In some embodiments, the mode of administration is subcutaneous or intramuscular. In addition, the compositions may be administered in conjunction with other treatment modalities such as substances that boost the immune system, various antibacterial chemotherapeutic agents, antibiotics, and the like.

Before exemplary embodiments of the present invention are described in greater detail, it is to be understood that this invention is not limited to any particular embodiment described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

The following Examples provide exemplary embodiments of the invention. Materials and methods for experiments presented in the examples are provided below. Data provided in the Examples are illustrated in FIGS. 1-14. Additional details about the experimental design of experiments and results can be found in the section entitled "Brief Description of the Drawings". Unless otherwise noted, all experiments in the following Examples were performed using chicken, bovine and human NK-lysin peptides. The assays were performed in triplicate and were repeated at three different times. Negative controls in all experiments were bacterial cells cultivated in the absence of NK-lysin peptides or NK-lysin peptide composition treatments.

Materials and Methods

Peptides

Mature peptides of bovine, human and chicken NK-lysin peptides synthesized by GenScript® (Piscataway, N.J.). HPLC was used to purify peptides up to 95%. Mass spectrometry analysis showed that the peptides had a mass of less than 1 Dalton of the theoretical value, as shown in

TABLE 1

Amino acid sequence and molecular weights of NK-lysin peptides

| Species | Amino Acid Sequence | M.W | SEQ ID NO |
|---|---|---|---|
| chicken | PDEDAINNALNKVCST-GRRQRSICKQLLKK | 3399.92 | SEQ ID NO: 01 |
| bovine | RPSKNVIIHVTSNVCSK-MGLWSILCNQMMK | 3419.16 | SEQ ID NO: 02 |
| human | PTQRSVSNAATRVCRT-GRSRWRDVCRNFMR | 3568.07 | SEQ ID NO: 03 |

Recombinant human interleukin-2 and kanamycin were obtained from Sigma Aldrich (St Louis, Mo., USA). A stock solution of kanamycin was prepared by dissolving in sterile water or 0.9% (w/v) NaCl and kept at −20° C. The stock solution was used within 2 weeks. The concentration was expressed as activity in micrograms per unit volume (μg/ml).

Bacteria Sample Preparation

The gram-positive bacterial strains utilized were *Streptococcus pyogenes* (ATCC 19615) and *Streptococcus mutans* (isolate obtained from a patient at King Abdul-Aziz hospital). The gram-negative bacterial strains used included *Salmonella typhimurium* (ATCC 14028), *Escherichia coli* (ATCC 11775), *Pseudomonas aeruginosa* (ATCC 9027), *Klebsiella oxytoca* (ATCC 49131), *Shigella sonnei* (ATCC 25931), and *Klebsiella pneumoniae* (patient isolate). Tryptic soy broth (TSB) was used to grow all bacterial strain overnight, after which the bacteria were washed using phosphate-buffered saline (PBS, NaCl 8 g/L, KCl 0.2 g/L, $Na_2HPO_4$ 1.4 g/L, $KH_2PO_4$ 0.24 g/L), and then diluted in the same buffer with 1/1000 TSB to an OD600 nm of 0.08-0.1 ($1\times10^8$) colony-forming units (CFU)/ml, which was determined after performing retrospective plate counts on tryptic soy agar. Unless otherwise noted, the experiments in the following examples employed this inoculum preparation apart from when minimum inhibitory and bactericidal concentrations were determined, which employed cells in Muller Hinton broth.

Antimicrobial Activity Assays

Minimum Inhibitory and Bactericidal Concentrations

The lowest inhibitory and bactericidal concentrations of NK-lysin of bovine, chicken and human peptides were obtained. The minimum inhibitory concentration (MIC) is defined as the lowest concentration of an antimicrobial ingredient or agent that is bacteriostatic (prevents the visible growth of bacteria). The minimum bactericidal concentration (MBC) is the lowest concentration of an antibacterial agent required to kill a bacterium over a fixed, somewhat extended period, such as 24 hours, under a specific set of conditions. The MBC is complementary to the MIC; whereas the MIC test demonstrates the lowest level of antimicrobial agent that greatly inhibits growth, the MBC demonstrates the lowest level of antimicrobial agent resulting in microbial death.

Mueller Hinton broth (MHB) comprising 0.01% v/v acetic acid (Sigma Aldrich; St Louis, Mo.) and 0.2% w/v bovine serum albumin (Sigma Aldrich). Equal concentrations of bacteria were plated in wells of standard tissue culture microplates at a density of $0.5\times10^8$ CFU ml-1 in MHB per well. Treatments were equivalent volumes (50 μl) of NK-lysin peptides in concentrations of 0 to 150 μg/ml, or no NK-lysin peptides for control wells. The treated plates were incubated at 37° C. and optical densities were determined for each well at 0 minutes, 1, 2 and 3 hours and after an overnight incubation. Wells were averaged to find $MIC_{50}$ values to denote the lowest peptide concentration that decreased growth of each microorganism by 50%.

Agar Disc Diffusion

Screening of NK-lysin peptides was carried out against gram-negative *S. typhimurium* (ATCC 14028) bacteria. Overnight cultivation of the bacteria was carried out at a temperature of 37° C. A bacterial suspension was created in 10 mM sodium phosphate buffer pH 7.0 having a density of ($2\times10^6$ CFU $ml^{-1}$) and plated on Muller-Hinton (MH) agar plates to inoculate. After the plates were dry, antibiotics discs of various concentrations (0 to 150 μg/ml) of antibiotic or NK-lysin peptides were applied to the surface of the inoculated plates. The plates were cultured overnight at 37° C. and observed for restriction of growth by determining the diameter of bacterial-free zones surrounding each disc. Ceftazidime antibiotic was employed as a positive control.

Colony Count Assays

Antimicrobial activity of NK-lysin peptides was assayed in cultures of *S. typhimurium* (ATCC 14028). The bacteria were maintained in tryptic soy broth at 37° C. and were grown to the mid-logarithmic phase prior to testing. To determine the activity of NK-lysin peptides, colony count assays were carried out. Bacteria were pelleted and then re-suspended in a 10 mM sodium phosphate buffer pH 7.0 and then diluted to a density of ($2\times10^6$ CFU $ml^{-1}$ in MHB. 50 μl of NK-lysin peptide were combined with an equal volume of bacterial culture and incubated at room temperature for 3 hours. A 1 µl sample of each culture was then diluted by 1000 (in 1 ml) and spread over MH agar plates. Colonies were counted after 24 hours at room temperature to determine the bacteria that survived.

Growth Kinetic Activity

The kinetic killing abilities of NK-lysin peptides were gauged in accordance with the Clinical Laboratory and Standard Institute (CLSI) broth micro-dilution technique presented by Wiegand and Hancock (2008). *Mueller Hinton broth comprising* 0.01% v/v acetic acid was prepared with 0.2% w/v bovine serum albumin, as above. Aerobic incubation of bacterial cells diluted to $0.5 \times 10^8$ CFU $ml^{-1}$ in MHB was carried out in microplates with the same volume (50 µl) of 2×MIC concentration of NK-lysin peptides. The plate was then incubated at room temperature. For each well, the optic densities were noted at 0 minutes and then at 1, 2, 3 and 4 hours. A distinct triplicate was used to repeat the kinetic potential of NK-lysin peptides thrice.

Synthesis and Characterization of Silver Nanoparticles

The chemicals and reagents used were of analytical grade. An aqueous solution of sodium borohydride was added to an aqueous solution of silver nitrate (0.05M) dropwise with constant stirring at room temperature. A precipitate was created from the drop-wise addition. Once the sodium borohydride was fully incorporated, the mixture was continuously stirred for another 10 minutes. The aqueous component was sampled to confirm the reduction of Ag+ ions by sodium borohydride within the solution.

TEM Examination of Silver Nanoparticles (AgNPs)

High resolution-transmission electron microscopy (HR-TEM; JEM-2100F; Jeol, Tokyo, Japan) instrument was used to differentiate the AgNPs at a high voltage of 200 KV. A Branson 1510 sonicator (NIST; Gaithersburg, Md.) was used to dissolve silver nano-powders in 90% ethyl alcohol solution. After this, the suspended Ag NPs were placed over a carbon-coated copper grid and high resolution-transmission electron microscopy was used to assess the particle size as well as the surface morphology.

Synergistic Effect of NK-Lysin Peptide and Silver Nanoparticles

The standard micro-dilution technique was used to determine MICs of NK-lysin peptide and of AgNPs. This method was also used to identify the synergistic impact of the mixture of NK-lysin and AgNPs. Dilution of the antibiotics was carried out in geometric progression. Serial dilutions of AgNPs using the MICs of AgNPs against the bacterial strain being examined. The silver concentrations were in the range of 0.6 to 5 mg/L, consistent with the bacterial strain employed. Aerobic incubation of the starting concentration of bacterial suspensions was fixed at a density of ($2 \times 10^6$ CFU $ml^{-1}$ in MHB and plated in microplates in an equal volume (50 µl) of 1×MIC concentration of an NK-lysin peptide. The plate was then incubated at room temperature and optic densities were obtained at 0 minutes, 1, 2 and 3 hours for each well.

Synergistic Effect of NK-Lysin Peptide and Human IL-2

The standard micro-dilution technique was used to measure the least-inhibitory concentration of NK-lysin peptide and Human IL-2 individually. This method was also used to measure the least-inhibitory concentration of the NK-lysin peptide mixed with IL-2. The 1×MIC of NK-lysin peptide against each bacterial strain was mixed with IL-2 (2 ng/ml). Aerobic incubation of the bacterial suspension adjusted to a density of ($2 \times 10^6$ CFU $ml^{-1}$ into MHB was carried out in microplate with the same volume (50 µl) of 1×MIC concentrations of NK-lysin peptide. The plate was then incubated at room temperature and the optic densities were noted at 0 minutes and then after 1, 2, 3, 4 and 24 hours for every well.

Assays Demonstrating the Mode of Action of NK-Lysin Peptides

Leakage of Intracellular Contents

The protocol of Carson et al. (*Antimicrob Agents Chemother.* 2002 June; 46(60:1914-20) was used with some changes to perform the assay for determining the loss of DNA/RNA. In short, 50 µl of bacteria was combined with the same volume of NK-lysin peptides at 2×MIC and then incubated at room temperature. Samples were harvested at 15, 30 and 60 minutes, diluted 1:10 and then filtered across 0.22 µm pores (Merck; Tullagreen, Ireland). The measurement of the O.D 260 nm of the filtrates was carried out over NanoDrop plate (Greiner Bio-One GmbH; Frickenhausen, Germany). The results were presented as a ratio to the original OD260 nm.

16S rRNA Amplification

Two universal primer sets 341F and 534 R were used to amplify 500 bp of 16s rRNA gene of *Salmonella typhimurium*. The forward primer had the following sequence: 5'-CCT ACG GGA GGC AGC AG-3' (SEQ ID NO:04), whereas the reverse primer had the following: 5'-ATT ACC GCG GCT GCT GGC-3' (SEQ ID NO:05). PCR amplification reactions were carried out in 50 µl of overall volume with a reaction mixture comprising 50 ng template DNA, 10 pmol each primer, 0.25 U Taq DNA polymerase, 10 mM Tris-HCl (pH. 9.0), 250 mM dNTPs mix, 30 mM KCl, 1.5 mM $MgCl_2$ in sterile nuclease-free water. The following cycling conditions were used to carry out the PCR reaction: pre-denaturing at 94° C. for 5 minutes, denaturing at 94° C. for 30 seconds, annealing at 60° C. for 30 seconds and extension at 70° C. for 1:30 minutes for 35 cycles and finally, an extension at 70° C. for 10 minutes. An analysis of the amplified fragments was carried out in 1.5% agarose gel stained with ethidium bromide. In addition, a 100 bp DNA ladder was added in agarose gel electrophoresis to indicate the size of amplificon products. A gel documentation system (Ultra-Violet Products Ltd; Upland, Calif.) was used to obtain images, and the software provided with the gel documentation system was used to determine the size of the amplicon.

Bacterial Lytic Potential

An assay described by Carson et al. (supra) was used with modifications to determine lytic potential of each NK-lysin. Screening of bacterial lytic potential of human and bovine NK-lysin peptides was carried out using two distinct bacterial inoculums, O.D600 (0.5) and O.D600 (1.0). Equal volumes of NK-lysin peptides (1×MIC) were combined with bacterial suspensions and plated in wells of microplates. The microplate was subsequently incubated at room temperature. A BioTek Instruments plate reader was used to measure the OD of each well of the microplate at various time intervals. NK-lysin peptides of corresponding concentrations in PBS were utilized as blanks. A ratio of OD600 nm at each time interval to the OD600 nm at 0 minutes was calculated and expressed as a percentage.

Bacterial Membrane Damage with Fluorescent Microscopy

*Salmonella typhimurium* membrane damage was determined by incubating $6.5 \times 10^6$ CFU of *Salmonella typhimurium* with 2×MIC of NK-lysin peptides in 10 mM phosphate buffer pH 7.0 at room temperature for one hour. Bacterial cells were stained with DAPI and PI for 1 hour, after which 10 µl of stained solution was added to a glass slide in a dark area. Slides were cover-slipped and examined by fluorescent microscopy (Nikon, Carl Zeiss; Oberkochen, Germany) was used to observe the membranes and detect any damage to the *S. typhimurium* membranes.

Detection of Beta-Lactamase Enzymes after NK-Lysin Peptides Challenge

Bacterial DNA Extraction

The following two gram-positive bacterial strains were used: *Streptococcus pyogenes* (ATCC 19615) and *Streptococcus mutans* (obtained from patient at King Abdul-Aziz hospital). The following five species of gram-negative strains are used: *Klebsiella oxytoca* (ATCC 49131), *Escherichia coli* (ATCC 11775), *Pseudomonas aeruginosa* (ATCC 9027), *Shigella sonnei* (ATCC 25931) and *Salmonella typhimurium* (ATCC 14028). Luria Bertani (LB) agar was used to grow the bacterial strains at room temperature overnight. A single colony was selected to inoculate 5 ml of LB broth, which was place in a shaking incubator at room temperature for 16 to 18 hours. After this, genomic DNA was obtained using a QIAGEN genomic DNA extraction kit (QIAGEN; Hilden, Germany) in accordance with the recommendations of the manufacturer.

Detection and Characterization of Beta-Lactamase Enzymes

PCR was performed to detect and characterize beta-lactamase (bla) genes using gene-specific oligonucleotide primers as shown in Table 2. Template nucleotide sequences were prepared as described in the above section Bacterial DNA Extraction.

TABLE 2

Specific forward (F) and reverse (R) primers (all reading 5' to 3') for PCR amplification of beta-lactamase genes. Amplicon size is shown in base pairs (bp).

| Gene | F/R | Nucleotide sequence | SEQ ID NO | bp |
|---|---|---|---|---|
| BLATem | F | ATGAGTATTCAACATTTCCG | SEQ ID NO: 06 | 869 |
|  | R | GACAGTTACCAATGCTTAATCA | SEQ ID NO: 07 |  |
| CTX-M1 | F | GACGATGTCACTGGCTGAGC | SEQ ID NO: 08 | 499 |
|  | R | AGCCGCCGACGCTAATACA | SEQ ID NO: 09 |  |
| TOHO1 | F | GCGACCTGGTTAACTACAATCC | SEQ ID NO: 10 | 351 |
|  | R | CGGTAGTATTGCCCTTAAGCC | SEQ ID NO: 11 |  |
| CTXM8 | F | CGCTTTGCCATGTGCAGCACC | SEQ ID NO: 12 | 307 |
|  | R | GCTCAGTACGATCGAGCC | SEQ ID NO: 13 |  |
| CTXM9 | F | GCTGGAGAAAAGCAGCGGAG | SEQ ID NO: 14 | 474 |
|  | R | GTAAGCTGACGCAACGTCTG | SEQ ID NO: 15 |  |
| Gyrase A | F | AAATCTGCCCGTGTCGTTGGT | SEQ ID NO: 16 | 344 |
|  | R | GCCATACCTACTGCGATACC | SEQ ID NO: 17 |  |
| QnrA | F | ATTTCTCACGCCAGGATTTG | SEQ ID NO: 18 | 516 |
|  | R | GATCGGCAAAGGTTAGGTCA | SEQ ID NO: 19 |  |
| QnrB | F | GATCGTGAAAGCCAGAAAGG | SEQ ID NO: 20 | 469 |
|  | R | ACGATGCCTGGTAGTTGTCC | SEQ ID NO: 21 |  |
| QnrD | F | CGAGATCAATTTACGGGGAATA | SEQ ID NO: 22 | 565 |
|  | R | AACAAGCTGAAGCGCCTG | SEQ ID NO: 23 |  |

TABLE 2-continued

Specific forward (F) and reverse (R) primers (all reading 5' to 3') for PCR amplification of beta-lactamase genes. Amplicon size is shown in base pairs (bp).

| Gene | F/R | Nucleotide sequence | SEQ ID NO | bp |
|---|---|---|---|---|
| QnrS | F | ACGACATTCGTCAACTGCAA | SEQ ID NO: 24 | 417 |
|  | R | TAAATTGGCACCCTGTAGGC | SEQ ID NO: 25 |  |

The PCR conditions include an initial denaturation at 94° C. for 5 min followed by 35 cycles; each for 30 s at 94° C., specific annealing temperature for 30 s with primers shown in Table 2 and extension for 30 s at 72° C., followed by final extension for 10 min at 72° C. PCR amplicons were electrophoretically separated in 1.5% gel, stained with ethidium bromide and visualized using a standard gel documentation system.

Characterization of Quinolone Resistance Genes

Genomic DNA was examined for presence of plasmid-mediated quinolone resistance genes and quinolone resistance determining region (QRDR) using primer sets shown in Table 2. The PCR conditions achieved include an initial denaturation at 94° C. for 5 min followed by 35 cycles; each for 30 s at 94° C., specific annealing temperature for 30 s and extension for 30 s at 72° C., followed by final extension for 10 min at 72° C. PCR amplicons were electrophoretically separated in 1.5% gel, stained with ethidium bromide and visualized using a standard gel documentation system.

Antiviral Activity of NK-Lysin Peptides

Cytotoxicity Experiments

Cytotoxicity of NK-lysin peptides was assayed in this study. Peptides were prepared at 80 μg/ml concentration using sterile deionized $H_2O$. Bi-fold serial dilutions were carried out starting with 100 μL of the dissolved peptides at 80 μg/ml. MA-104 cell monolayers were used to inoculate 100 μL of each dilution. Cell morphology of the bacteria was observed daily for 6 days with an inverted light microscope to evaluate toxicity of the peptides.

Rotavirus and Cell Culture Preparation

Rotavirus (strain SA-11) was activated with 10 μg/mL trypsin before propagation on MA-104 cells derived from kidney cells of African rhesus monkey. MA-104 cells were cultivated in tissue culture flasks in the presence of less than 5% $CO_2$ at 37° C. in Dulbecco's Minimal Essential Medium (DMEM) (Sigma-Aldrich) The DMEM included 1% antibiotic antimycotic solution and 10% heat inactivated fetal bovine serum (A5955, Sigma-Aldrich). Centrifugation of rotavirus was performed at 300×g for 5 mins in order to purify by removal of cell debris. The supernatant was utilized as a stock suspension of virus after filtration through 0.2 μm membrane. The stock virus contained $10^6$-$10^7$ TCID50 per mL and was stored at −80° C. for future use.

Antiviral Efficacy Experiment

Figure 2:
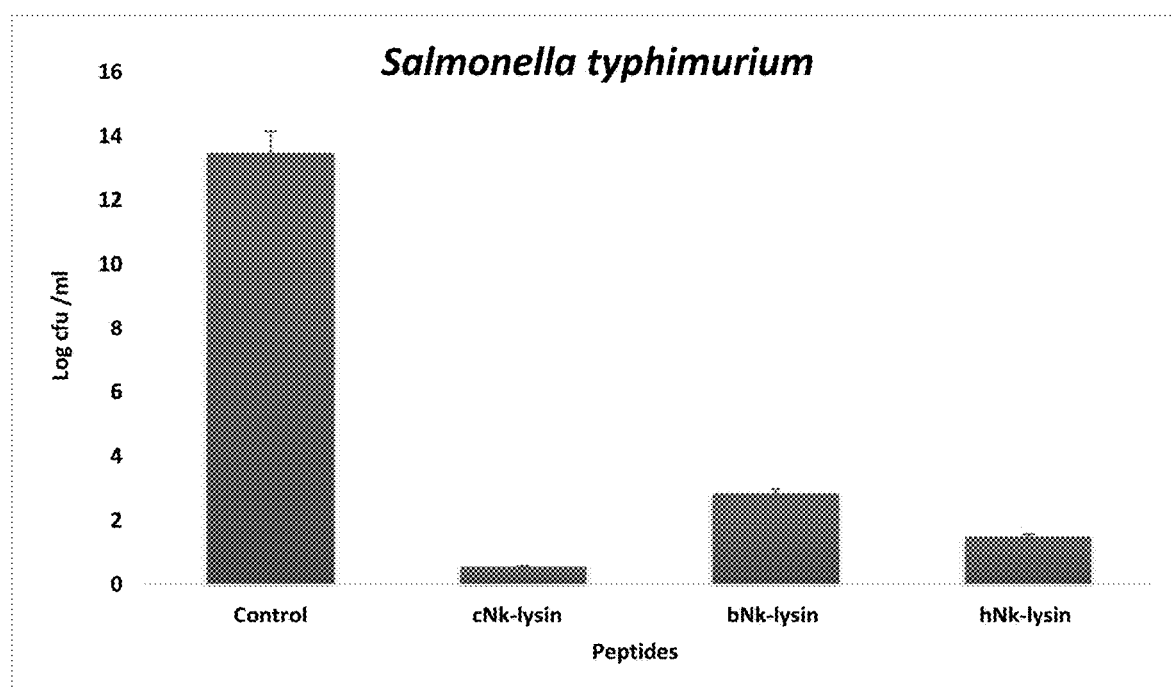
FIG. 2 shows the results of colony counting assays of NK-lysin peptides of chicken, bovine, human against *S. typhimurium*. Data presented as means (±SD) of three independent repeats in triplicate.

In order to activate infectivity, rotavirus was placed in a solution of 10 μg/mL trypsin at 37° C. for 30 min. A 100 μl aliquot of the activated rotavirus sa-11 was mixed with and equal volume of 80 μg/ml NK-lysin peptides for a final rotavirus concentration of 1×$10^6$ TCID50/ml. The rotavirus and NK-lysin peptide mixture was first incubated for at 37° C. for 1 hour. Serial dilutions of rotavirus and rotavirus+ peptide mixtures were prepared. Aliquots 100 μl of the 10-fold serial dilutions were then added to 96-well tissue culture plates comprising monolayers of MA-104 cells at a density of approximately 5.0×$10^4$ cells per well. Eight wells were used for each sample to make sure sufficient assay precision was achieved. The microplates were incubated for 5 days at 37° C. under 5% $CO_2$ atmosphere. During the 5-day incubation, cells were monitored daily under a microscope to check for a cytopathic effect (CPE). A tissue culture infectious dose (TCID) was the infectious dose/mL of tissue culture equal to 50 percent of wells showing CPE at a specific dilution and was expressed as the TCID50 for that dilution. The highest dilutions in which 50% or higher wells were read as the TCID50.

are shown in FIG. 2 for *Salmonella typhimurium* treated with chicken, bovine or human NK-lysin to establish a value for colony forming units for each. For example, at 30 μg/ml concentration, chicken NK-lysin decreased the colony number by approximately 10-fold. Bovine NK-lysin at 25 μg/ml concentration around 8.6-fold decline in bacterial survival. A higher concentration of human NK-lysin peptide (70 μg/ml) led to decrease bacteria growth by 4.6-fold. The data for the activity of all three NK-lysin peptides at all concentrations is summarized in Table 3.

TABLE 3

Antimicrobial activity of chicken, bovine and human NK-lysin peptides against gram-positive and gram-negative bacteria, with kanamycin as an antibiotic control for comparison.

| Bacterial strain | Chicken NK-lysin | | Bovine NK-lysin | | Human NK-lysin | | Kanamycin | |
|---|---|---|---|---|---|---|---|---|
| | MIC (μg/ml) | MBC (μg/ml) | MIC (μg/ml) | MBC (μg/ml) | MIC (μg/ml) | MBC (μg/ml) | MIC (μg/ml) | MBC (μg/ml) |
| Gram-negative strains: | | | | | | | | |
| *S. typhimrium* ATCC 14028 | 15 ± 0.098 | 30 ± 0.10 | 15 ± 0.10 | 25 ± 0.12 | 15 ± 0.090 | 70 ± 0.092 | 62.5 ± 0.00 | 62.5 ± 0.00 |
| *K. Pneumonia* (isolate) | 15 ± 0.030 | 25 ± 0.010 | 15 ± 0.03 | 25 ± 0.010 | 15 ± 0.040 | 15 ± 0.040 | 31.25 ± 0.00 | 31.25 ± 0.00 |
| *E. coli* ATCC 11775 | 15 + 0.012 | 25 ± 0.010 | 15 ± 0.012 | 25 ± 0.010 | 15 ± 0.014 | 25 ± 0.012 | 15.62 ± 0.011 | 15.62 ± 0.00 |
| *K. oxytoca* ATCC 49131 | 15 ± 0.015 | 25 ± 0.10 | 15 ± 0.015 | 25 ± 0.10 | 15 ± 0.012 | 15 ± 0.012 | 31.25 ± 0.00 | 31.25 ± 0.00 |
| *P. aeruginosa* ATCC 9027 | 15 ± 0.012 | 25 ± 0.013 | 15 ± 0.012 | 25 ± 0.013 | 15 ± 0.010 | 15 ± 0.010 | 62.5 ± 0.00 | 62.5 ± 0.00 |
| *Sh. sonnei* ATCC 25931 | 15 + 0.033 | 25 ± 0.010 | 15 ± 0.033 | 25 ± 0.010 | 15 ± 0.025 | 25 ± 0.012 | 7.81 ± 0.026 | 7.81 ± 0.026 |
| Gram-positive strains: | | | | | | | | |
| *St. pyogenes* ATCC 19615 | 15 ± 0.00 | 25 ± 0.010 | 15 ± 0.00 | 25 ± 0.010 | 15 ± 0.00 | 25 ± 0.010 | 62.5 ± 0.00 | 62.5 ± 0.00 |
| *St. mutans* (isolate) | 15 ± 0.00 | 15 ± 0.00 | 15 ± 0.0 | 15 ± 0.0 | 15 ± 0.010 | 25 ± 0.012 | 62.5 ± 0.023 | 62.5 ± 0.23 |

MIC = minimum inhibitory concentration;
MBC = minimum bactericidal concentration Statistical Analysis The experiments were carried out in multiples of three and were repeated at three different time. The data are presented as the means with standard error. A two-tailed test was performed on the data using Microsoft Excel 2020.

Example 1

Minimum Inhibitory and Bactericidal Concentrations

This Example establishes the MIC and MCB, and further demonstrates the relative antibacterial activity of three different NK-lysin peptides from human, chicken, and bovine activity directed against gram-negative and gram-positive bacteria.

Figure 1B:
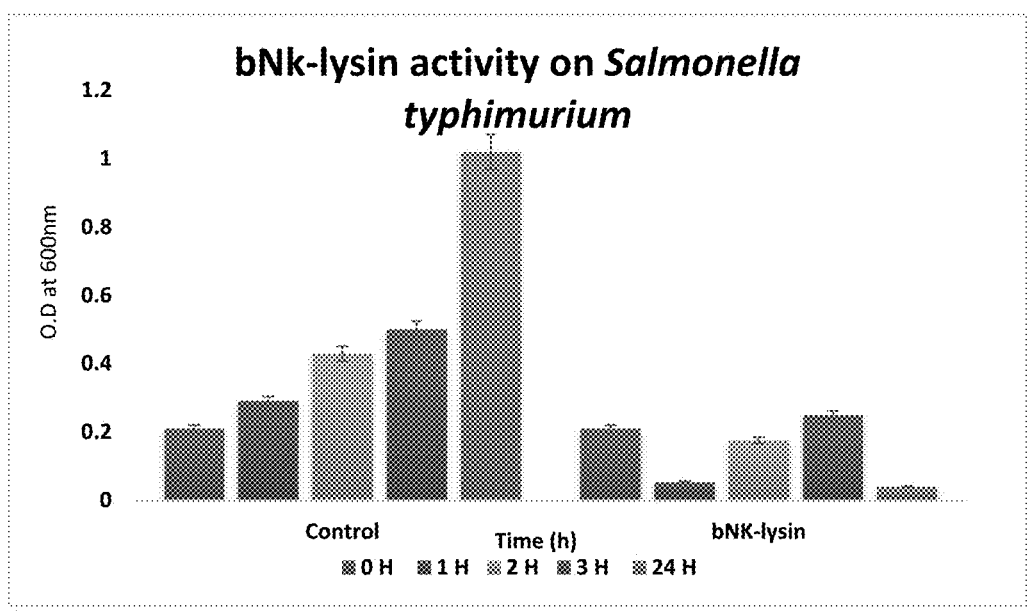
Figure 1C:
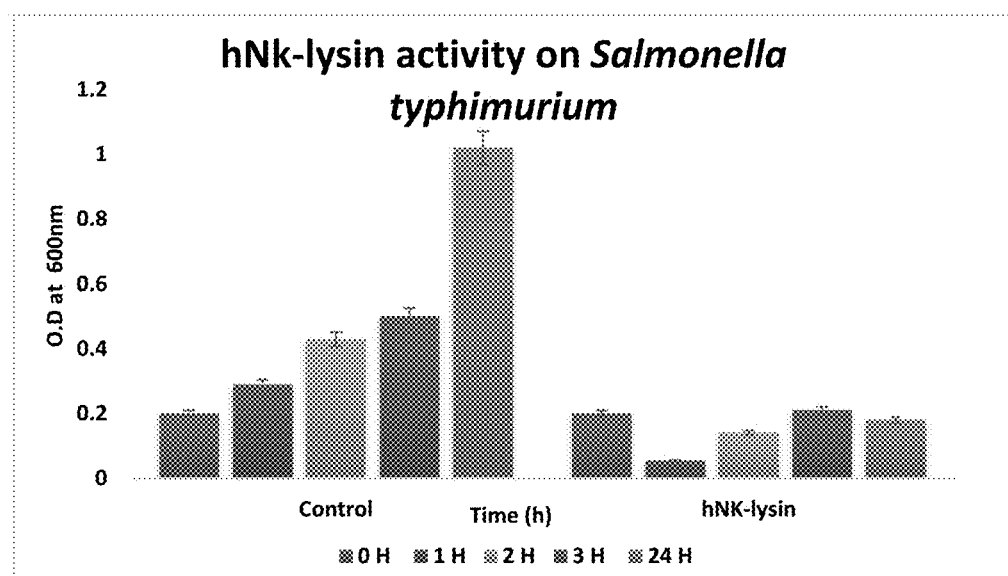

FIGS. 1A, 1B and 1C show the NK-lysin activity against *Salmonella typhimurium* using chicken, bovine or human NK-lysin peptides, respectively. All three peptides killed more than 95% of *S. typhimurium* compared to the no-peptide control at the time point measured (1 hr) post-initial incubation and exposure.

Colony Count Assays

Figure 3A:
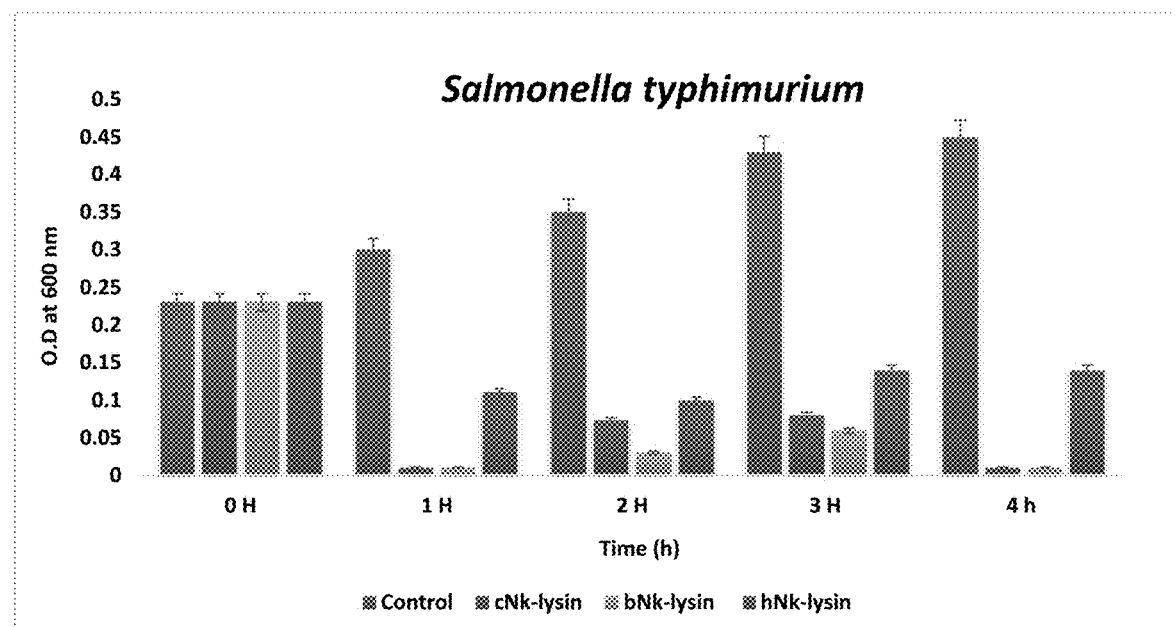
FIGS. 3A-3H show growth kinetic activities of 2×MIC of chicken, bovine and human NK-lysin peptide against: *Salmonella typhimurium* (ATCC 14028) in FIG. 3A; against *Streptococcus mutans* (isolate) shown in FIG. 3B; against *Escherichia coli* (ATCC 11775) in FIG. 3C; against *Klebsiella oxytoca* (ATCC 49131) in FIG. 3D; against *Pseudomonas aeruginosa* (ATCC 9027) in FIG. 3E; against *Klebsiella Pneumonia* (isolate) in FIG. 3F; against *Shigella sonnei* (ATCC 25931) in FIG. 3G and *Streptococcus pyogenes* (ATCC 19615) in FIG. 3H. Data presented as means (±SD) of three independent repeats in triplicate.
Figure 3B:
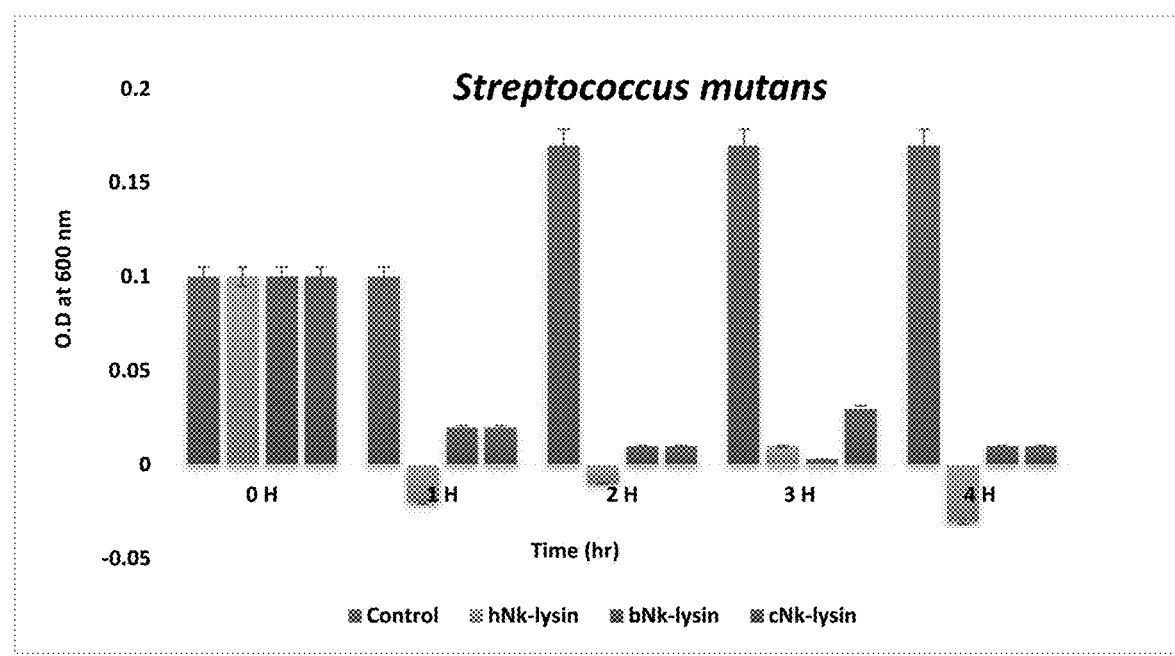
Figure 3C:
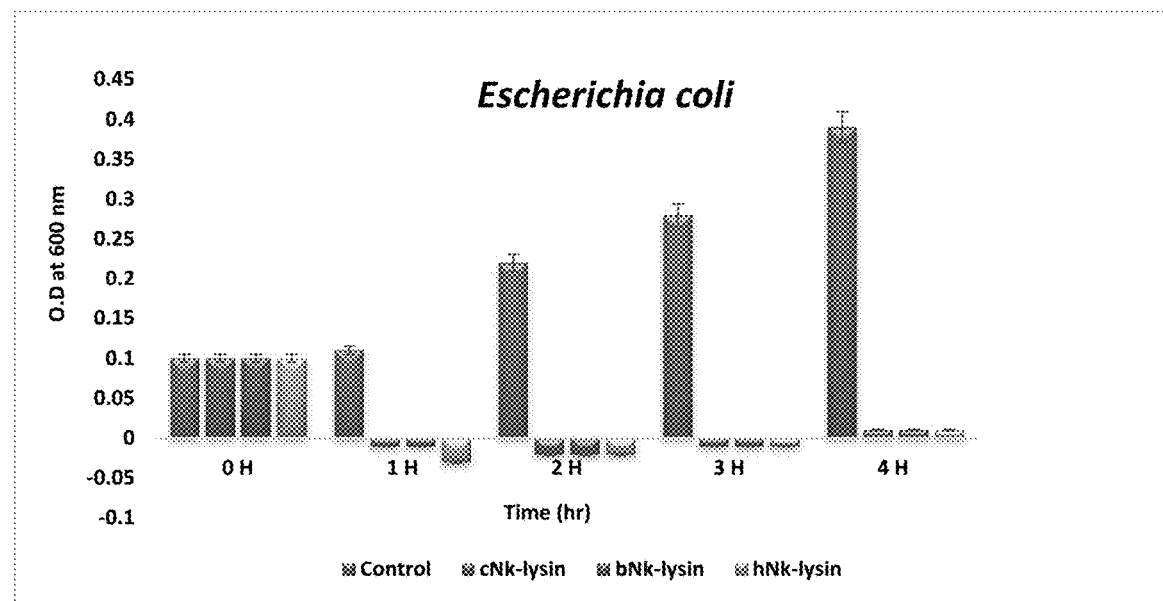

The colony forming unit of *Salmonella typhimurium* was determined using NK-lysin peptides. Aliquots of *S. typhimurium* treated with the NK-lysin peptides were plated and counted after incubation in the presence of the peptides. Colony counts for an exemplary concentration of peptides FIG. 3A illustrates that all three NK-lysin peptides showed strong antibacterial activity against *Salmonella typhimurium* at a concentration of 15 μg/ml at three hours. The human NK-lysin peptide exhibited stronger antibacterial potential than peptides from chicken and bovine species after second and third hours of exposure and produced more than 60% and 50% reduction of bacterial survival at time intervals assayed. NK-lysin peptides of bovine and chicken exhibited strong antimicrobial activity (15 μg/ml) with less than 5% survival rate overnight, while human peptide displayed (82% killing) overnight. The same assay was performed against additional bacterial strain, including *Streptococcus mutans*, shown in FIG. 3B; *E. coli*, shown in FIG. 3C; *Klebsiella oxytoca*, shown in FIG. 3D; *Pseudomonas aeruginosa*, shown in FIG. 3E; *Klebsiella pneumonia*, shown in FIG. 3F; *S. sonnei*, in FIG. 3G and *Streptococcus pyogenes*, shown in FIG. 3H. Results are also summarized in Table 3, above. As shown, the NK-lysin peptides exhibited a wide range of activity against both gram-positive and gram-negative pathogens. The MIC and MBC values of chicken NK-lysin peptide ranged from 15 to 30 μg/ml displayed the maximal activity against all bacteria tested in the assays. However, similar results were recorded for bovine and human NK-lysin peptides, showing maximal activity of MIC at 15 μg/ml and MBC at 15-70 μg/ml, respectively. Notably, all NK-lysin peptides were found to be more efficient regarding bacterial inactivation as compared to the reference antibiotic, kanamycin, except in the case of *Shigella sonnei*, wherein kanamycin was shown to be more potent than the NK-lysin peptides.

Results of these assays showed that killing of bacteria by the NK-lysin peptides followed a dose-dependent pattern. Bacterial survival was less than 50% with treatment of each of the three peptides at low concentration (0.350 µg/ml). Chicken and bovine NK-lysin peptides displayed stronger antibacterial effects than human NK-lysin peptides under these test conditions. Accordingly, all three peptides demonstrated efficient antibacterial activities across a wide range of peptide concentrations.

Example 3

Growth Kinetic Activity

To observe time-dependent changes in the bacterial growth, the bacterial concentration and growth inhibition rates were further evaluated by measuring the OD at 600 nm at different time points shown in FIGS. 3A-3H. The untreated bacterial growth curve reached the exponential phase rapidly and then followed a regular pattern comprising of a period of lag, an exponential phase followed by a stabilization phase.

The growth of *Salmonella typhimurium* was decreased in lag phase at the first one hour, then enter exponential phase at the second hour with less than 20% survival rate for chicken and bovine NK-lysin peptides. The same scenario was detected at the third hour for both peptides. Complete inhibition was achieved after 4 hr of incubation at 2×MIC of chicken and bovine NK-lysin.

For human NK-lysin peptide first hour, the growth of *Salmonella typhimurium* declined to 30% at lag phase, then was less than 40% when read at the 2 hr and 3 hr time points. At a concentration of 2×MIC, the bacterial growth was less than 25% after incubation for 4 hr. Thus, bacterial growth inhibition not only depended on the peptide type but also on peptide concentration.

Figure 3D:
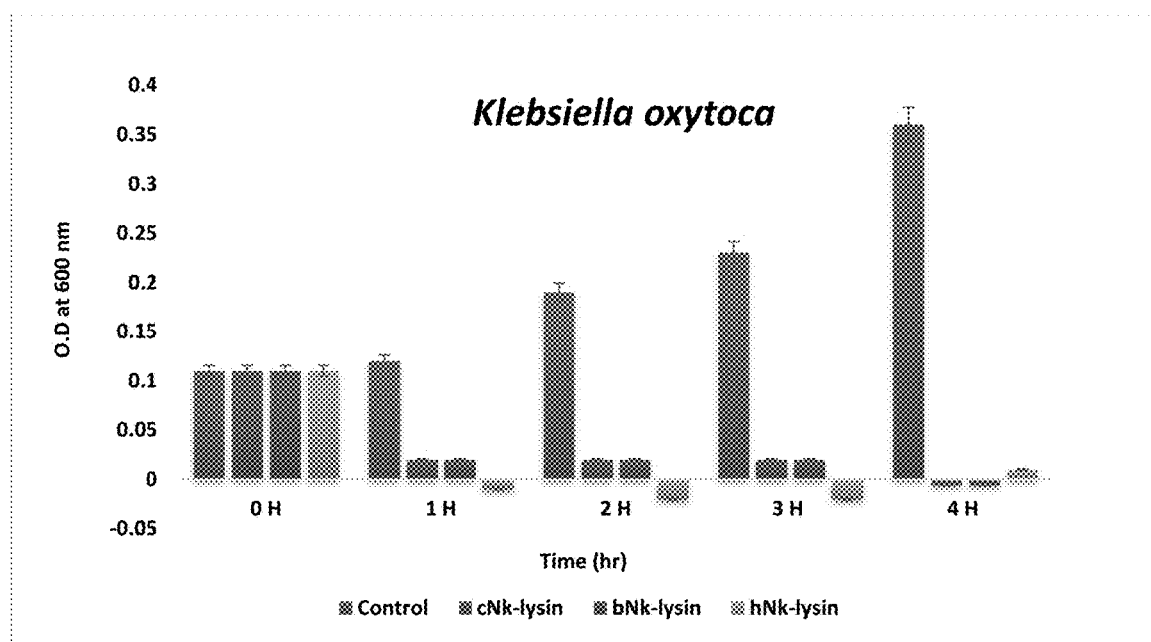
Figure 3E:
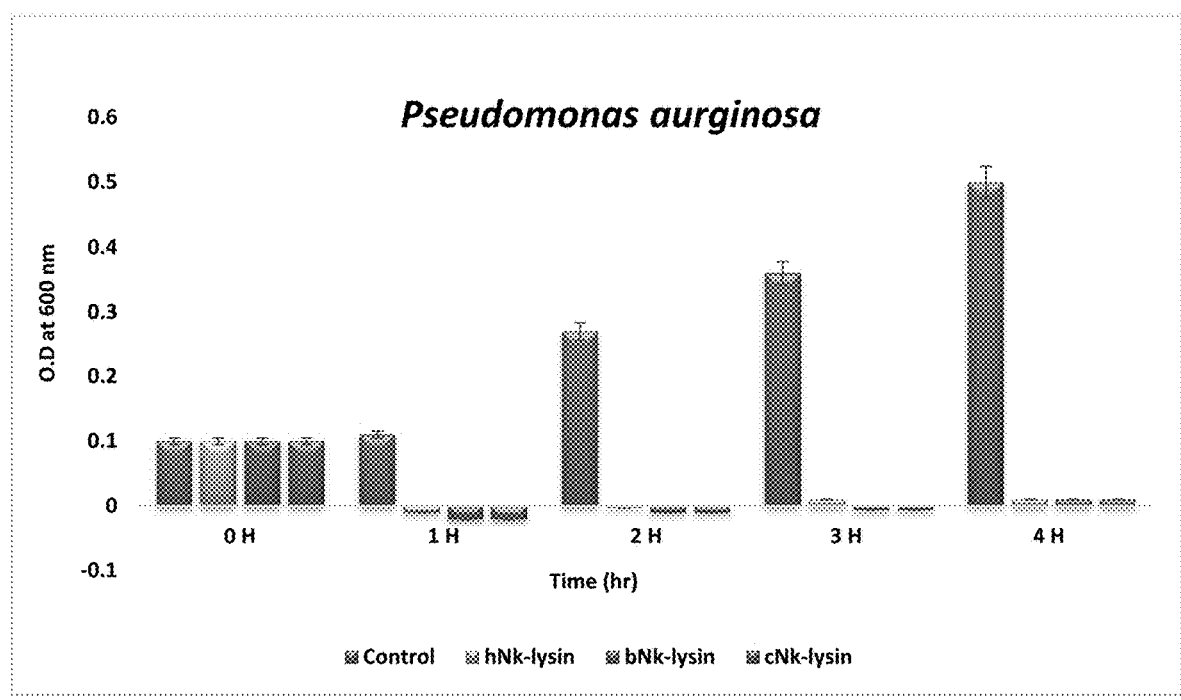
Figure 3F:
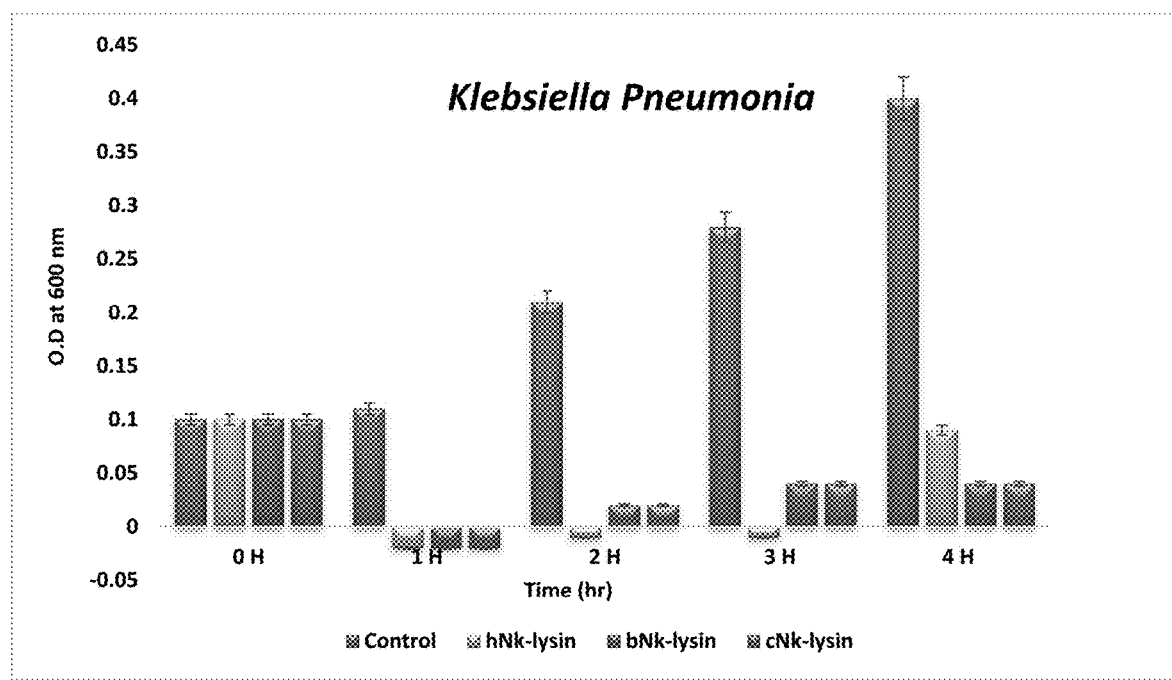
Figure 3G:
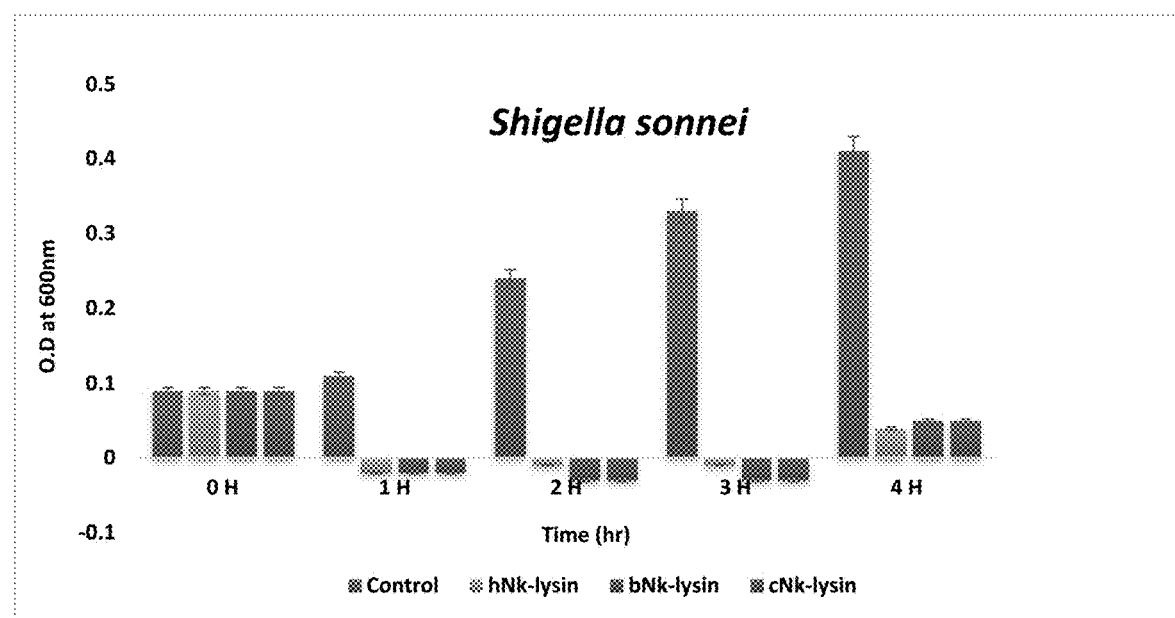
Figure 3H:
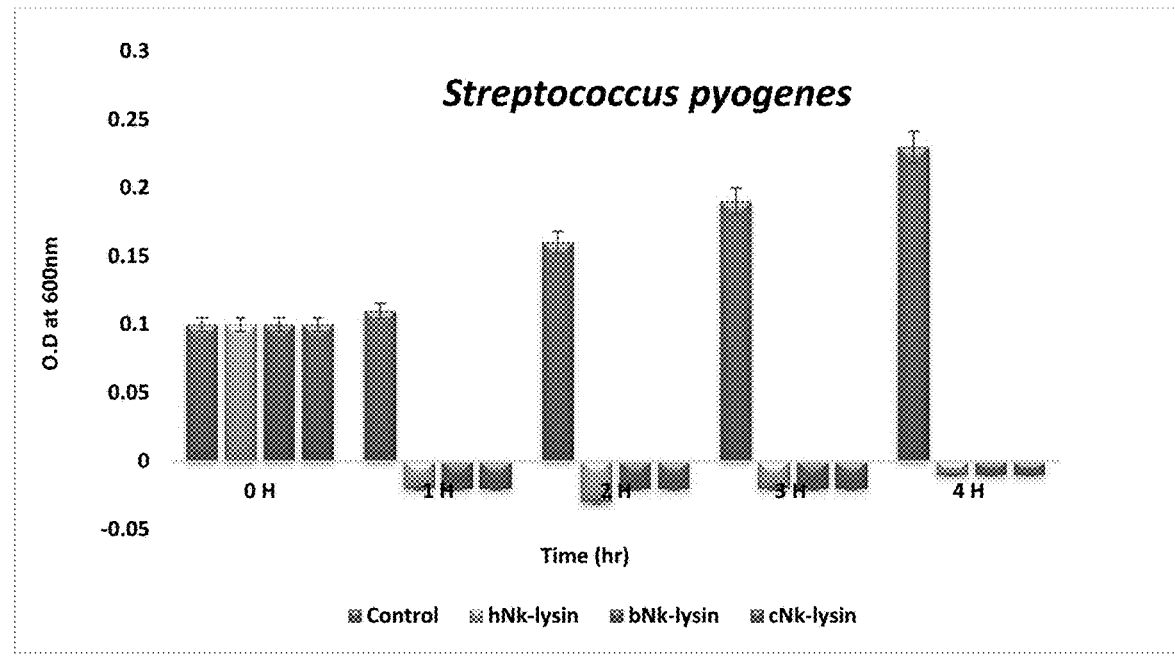

In the case of *Klebsiella oxytoca*, complete inhibition of growth was achieved after 4 hr of incubation with the three NK-lysin peptides, as shown in FIG. 3D. This held true for *Streptococcus mutans* also, in that the dead phase occurred dramatically after exposure of NK-lysin peptides; however, the chicken NK-lysin peptide demonstrated more potent activity than bovine or human NK-lysin peptides, shown in FIG. 3B, based on the kinetic activity and greatest level of efficacy in a time dependent manner regarding MIC or MBC. Kinetic growth activity was completely inhibited by incubation with NK-lysin peptides for *E. coli* (FIG. 3C), *Klebsiella aeruginosa* (FIG. 3E), *Klebsiella pneumoniae* (FIG. 3F), *Shigella sonnei* (FIG. 3G), and *Streptococcus pyogenes* (FIG. 3H) by the 3 hr readings.

Example 4

Agar Disc Diffusion

Chicken, bovine and human NK-lysin peptides displayed antibacterial activity against gram-negative *S. typhimurium* in presence of two of the most commonly used antibiotic discs (gentamicin and ceftazidime). The results showed a strong clear zone diameter of 23 mm for chicken and bovine NK-lysin peptides, while human peptide produced a 21 mm clear diameter and was similar in size to the clear zone diameter produced by ceftazidime antibiotic. The largest zone diameter was recorded regarding gentamicin antibiotic with 28 mm.

Example 5

Combination of NK-Lysin Peptides and AgNPs

Figure 4:
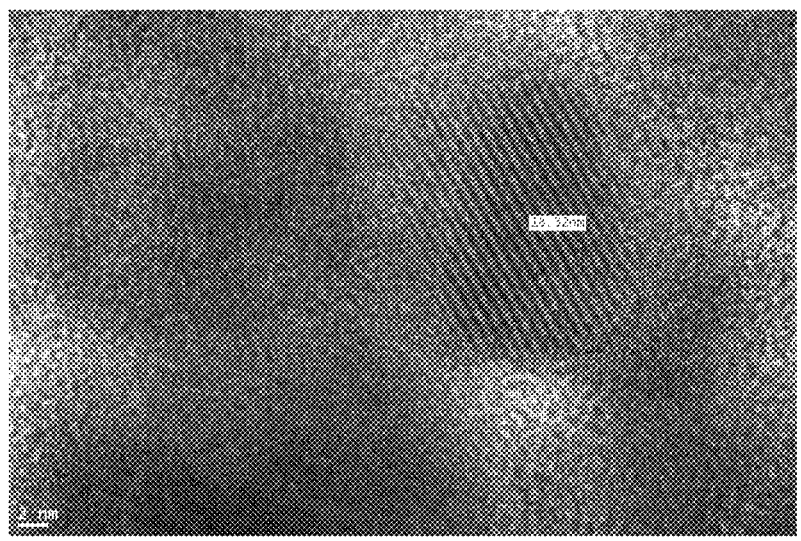
FIG. 4 shows a representative TEM micrograph of the aggregation of suspended silver nanoparticles in water that are spherical in shape and range from 18±5 nm in diameter (bar=2 nm) demonstrating exemplary characterization of the prepared silver nanoparticles.

AgNPs were prepared and analyzed under high magnification. Images of AgNPs acquired by using high resolution transmission electron microscope (TEM) showed that the nanoparticles were spherical in shape with the most obvious size being 18.5 nm. An exemplary TEM image of the AgNPs is shown in FIG. 4, showing crystallographic planes of silver that were apparent at high resolution. These results were in agreement with Anwar et al. (*Drug Devel Indust Pharma.* 2015; 41:43-50) who reported an AgNPs lattice space of approximately 0.24 nm.

Figure 5:
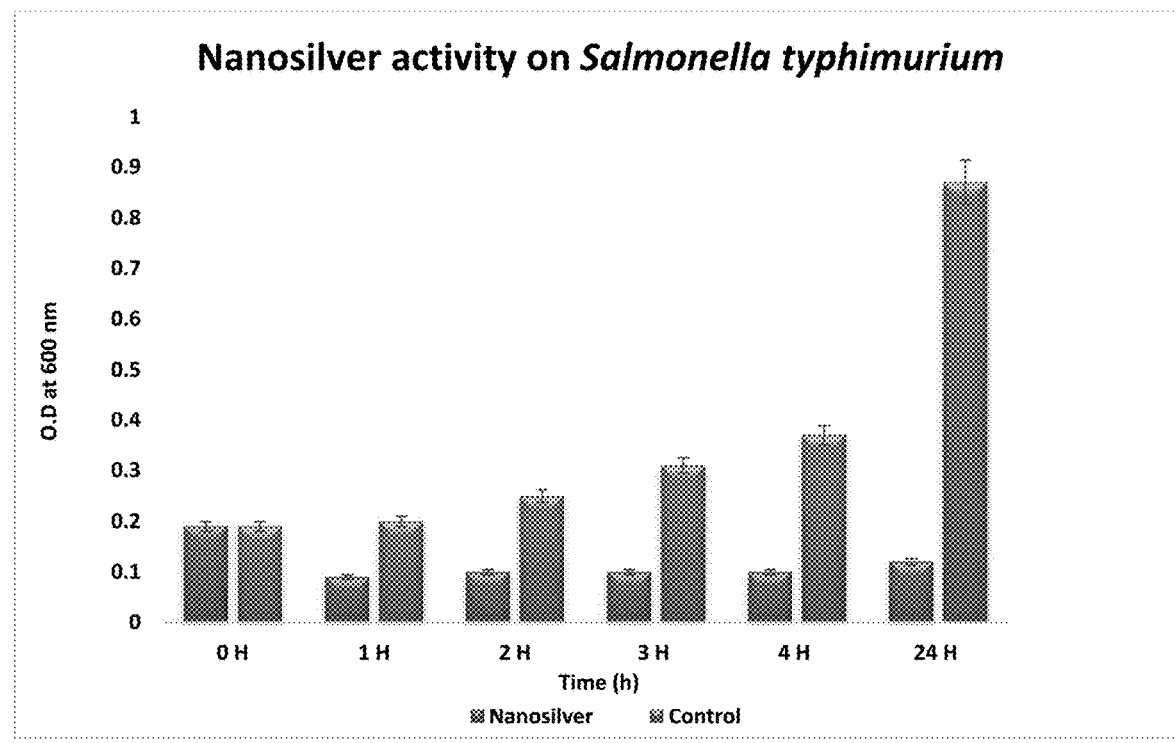
FIG. 5 shows antimicrobial activity of nanosilver particles against *Salmonella typhimurium* (ATCC 14028). Data presented as means (±SD) of three independent repeats in triplicate.
Figure 6A:
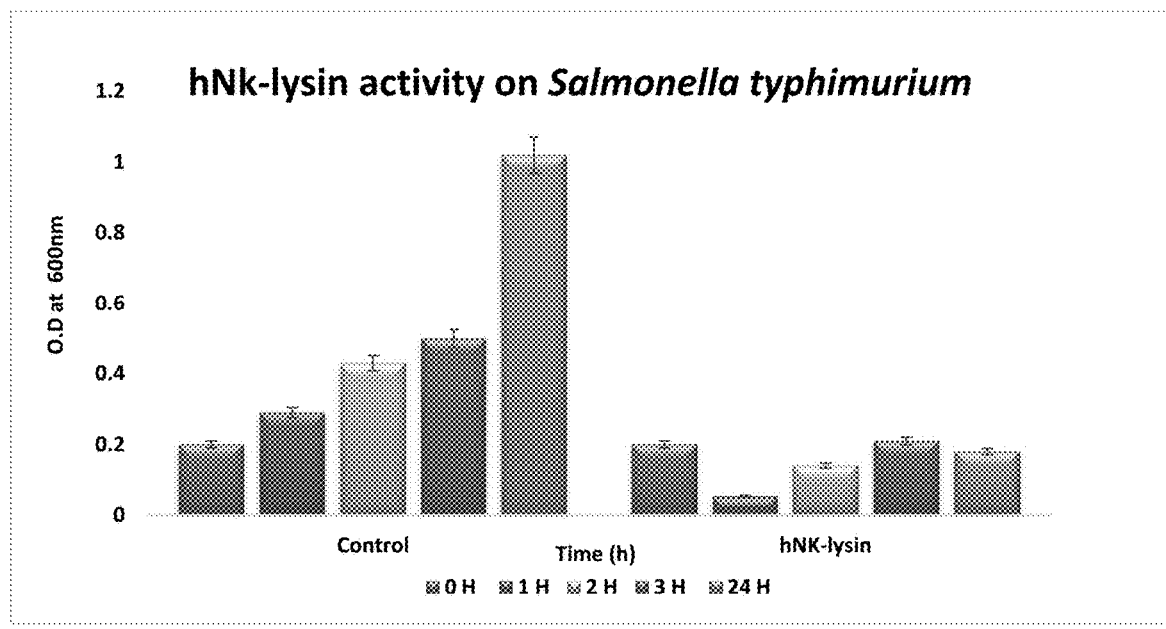
FIGS. 6A and 6B show the activity of human of Nk-lysin peptide alone and with nanosilver particles (hNK-lysin+Nanosilver) against *Salmonella typhimurium* (ATCC 14028).
Figure 6B:
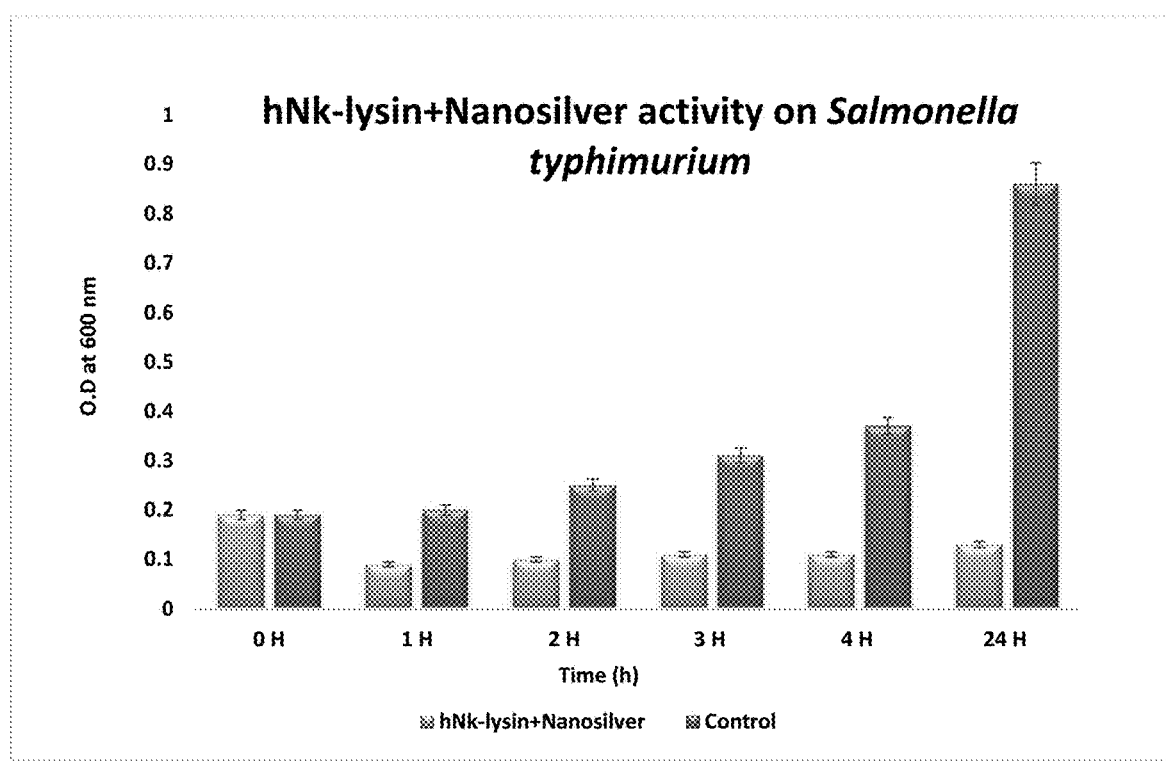
Figure 7:
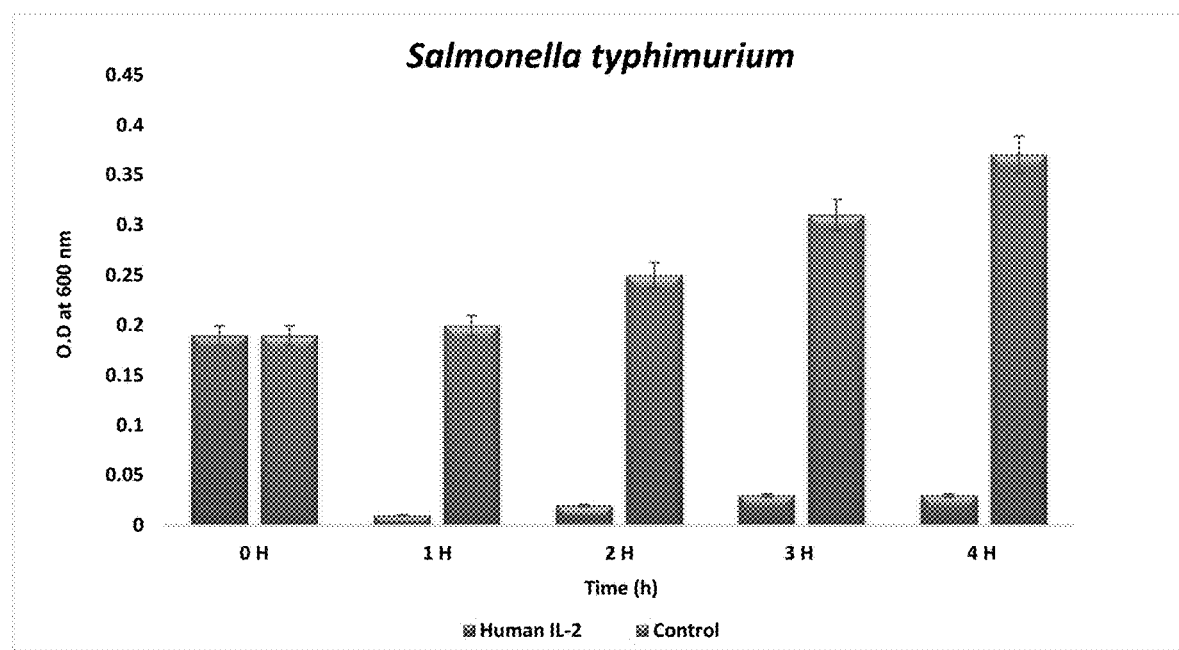
FIG. 7 shows antimicrobial activity of human IL-2 against *Salmonella typhimurium* (ATCC 14028). Data presented as means (±SD) of three independent repeats in triplicate.

The antibacterial activity against *S. typhimurium* using the 18.5 nm spherical AgNPs alone is depicted in FIG. 5. Potent antibacterial activity was observed at the 1-hour time point post-onset of exposure to AgNPs and continued the same trend at 2 and 3 hours and with overnight incubation at 24 hours. As seen in earlier studies, human NK-lysin was also effective at suppressing or inhibiting growth of *S. typhimurium*, as measured a 1, 2, 3 and 24 hours, shown in FIG. 6. The combination of AgNPs and NK-lysin peptide exhibited strong effect against *S. typhi* at time intervals as indicated in FIG. 7. While AgNPs and NK-lysin peptides each possess activities and antibacterial effects that may be additive, the amount of inhibition achieved with the combination did not exceed the effect of AgNPs alone. Thus, the results demonstrated that AgNPs can serve as a combination therapeutic agent in order to treat infectious diseases caused by bacteria.

Example 6

Combination of NK-Lysin Peptides and Human IL-2

Figure 8A:
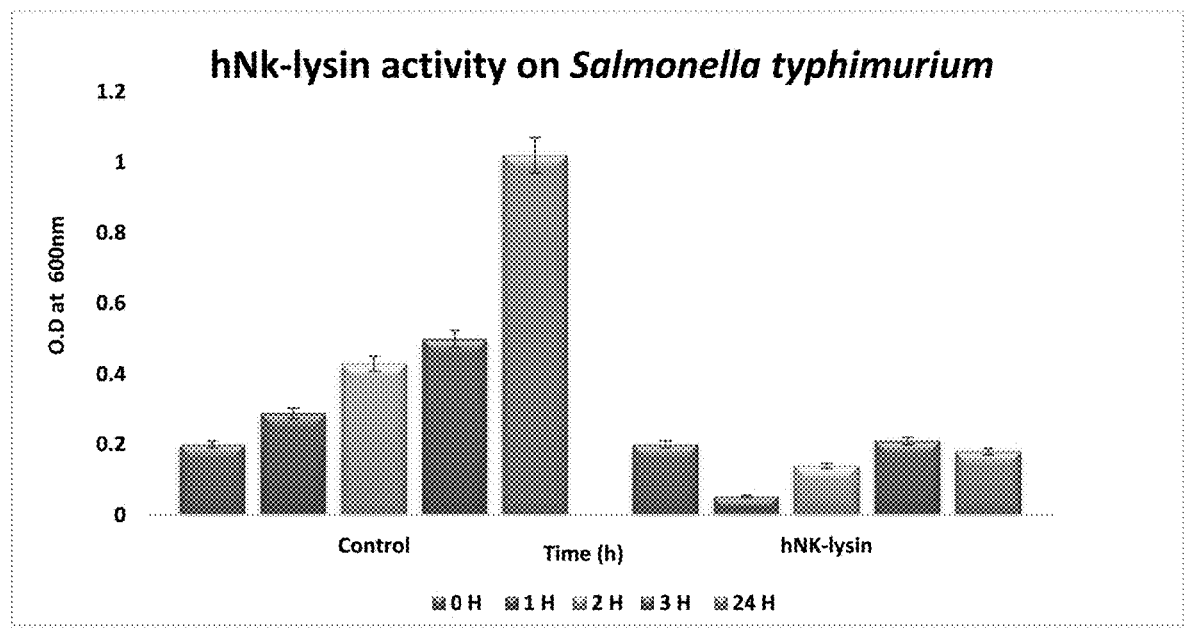
FIGS. 8A and 8B show the activity of peptides against *Salmonella typhimurium* (ATCC 14028).
Figure 8B:
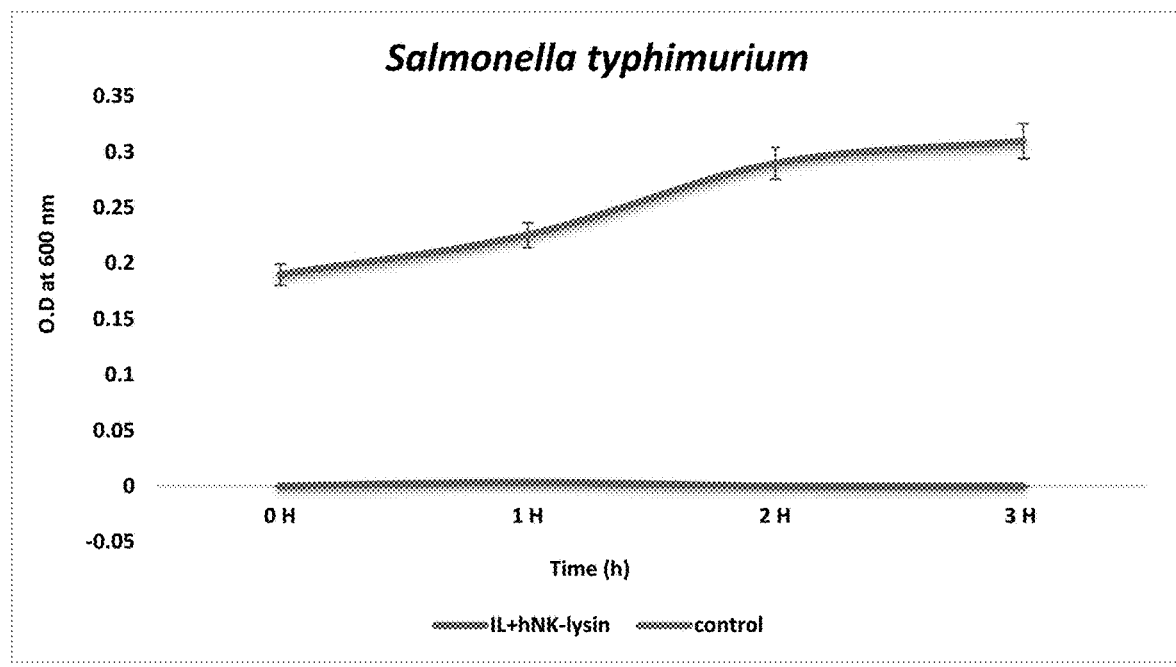
Figure 9:
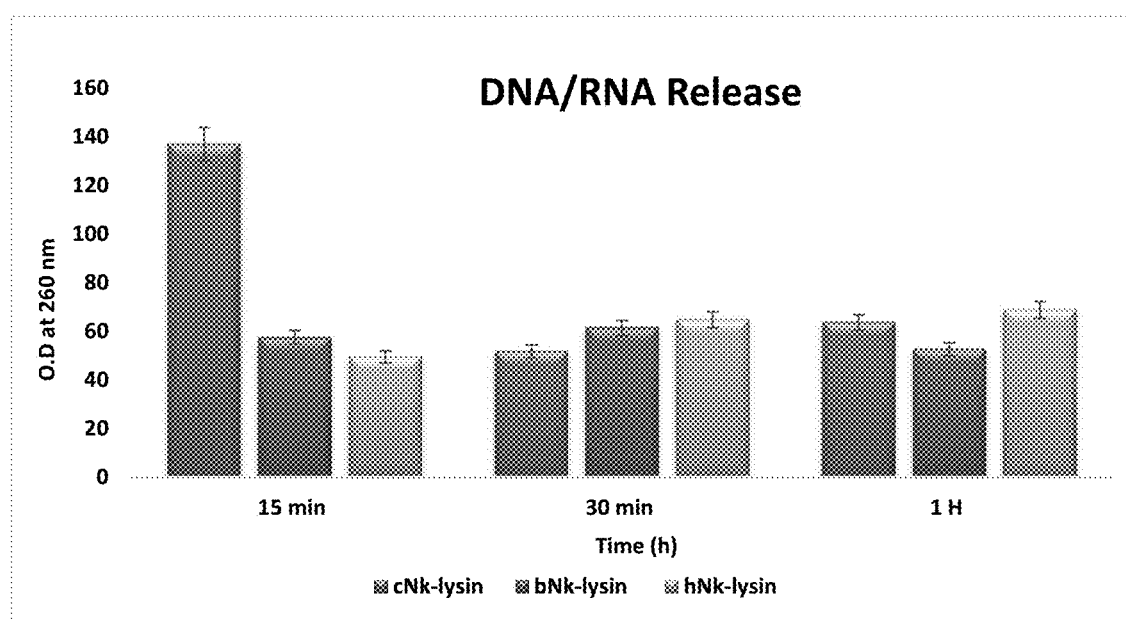
FIG. 9 shows DNA/RNA released from *Salmonella typhimurium* (ATCC 14028) bacterial cells after incubation with chicken, bovine or human NK-lysin peptides at 37° C. for 15, 30 and 60 minutes. Data presented as means (±SD) of three independent repeats in triplicate.
Figure 10A:
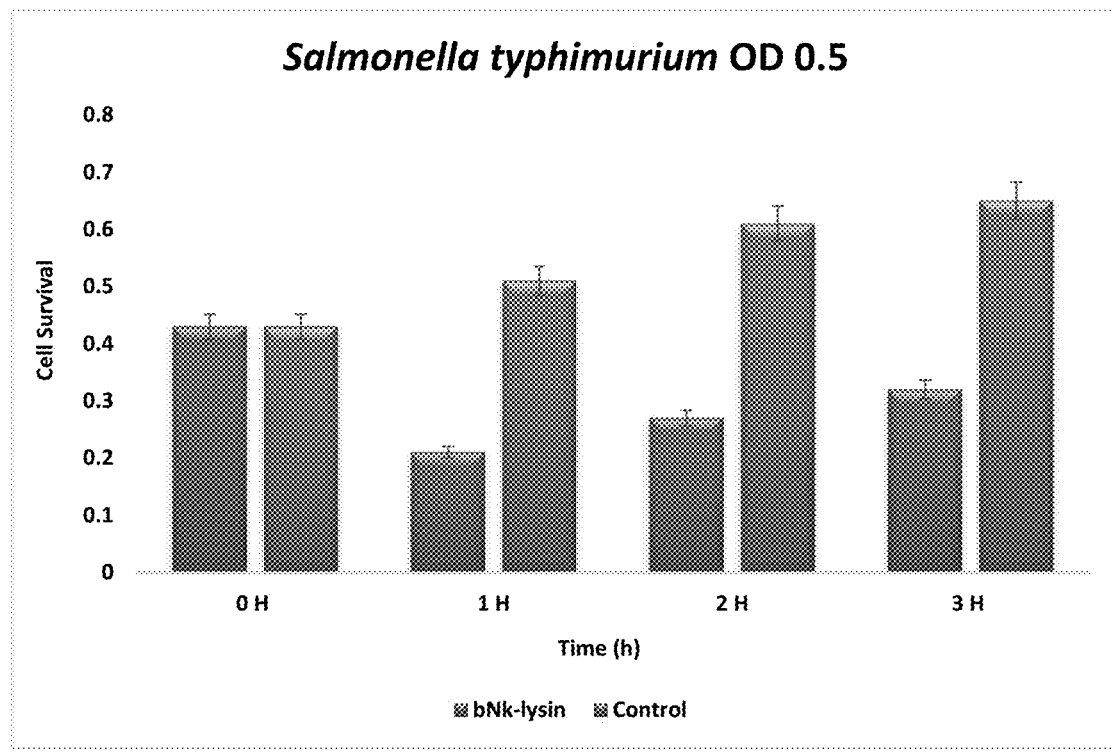
FIGS. 10A and 10B show the bacterial lytic effect of 1×MIC bovine NK-lysin peptide against *Salmonella typhimurium* (ATCC 14028) at two different inoculum concentrations. Data presented as means (±SD) of three independent repeats in triplicate.
Figure 10B:
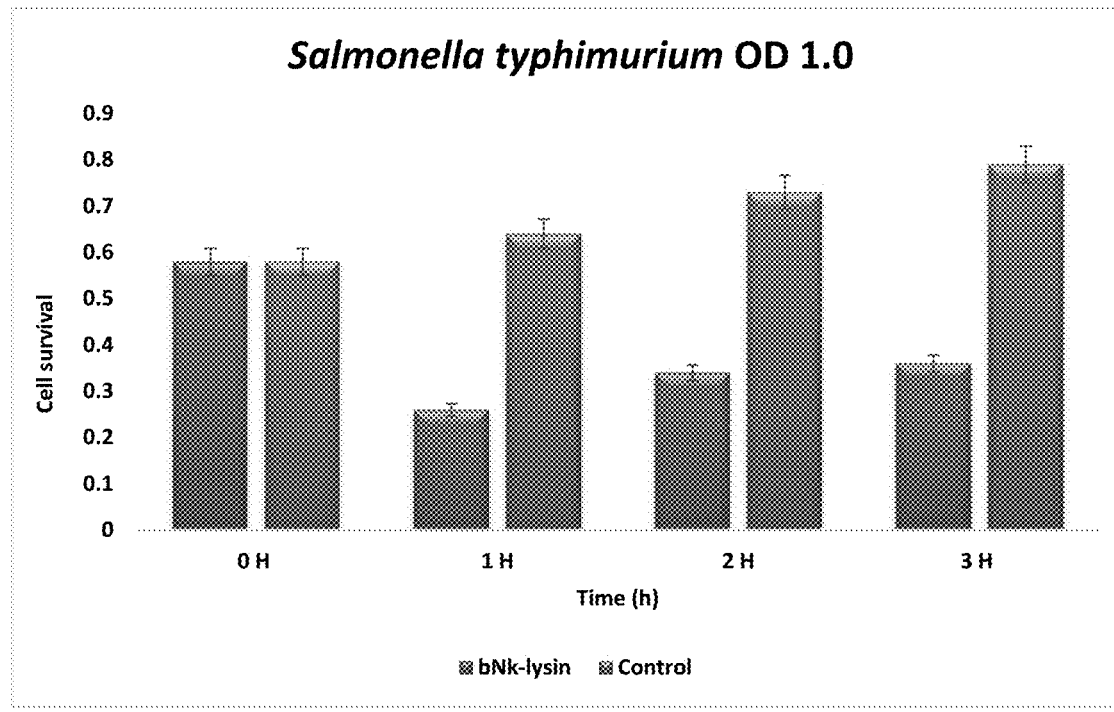

An inhibition assay was conducted to determine the antibacterial activity of human IL-2 alone against *S. typhimurium*. The results of these inhibition assays are depicted in FIG. 8, which shows that the antibacterial action of IL-2 was maintained over the 24 hours of assay time, with the maximum potential for antibacterial activity after 3 hours with IL-2 treatment compared to untreated control cultures. As shown earlier, human NK-lysin peptides also inhibited growth of *S. typhimurium*, shown in FIG. 9. Inhibition assays of the combined activity of IL-2 and NK-lysin peptide were also performed against *S. typhimurium*, as shown in FIG. 10. The results demonstrated that IL-2 and NK-lysin peptides are equipotent in their antibacterial activity when each is tested alone, but the combination of IL-2 and NK-lysin peptides appears to be synergistic in effectiveness, resulting in complete inhibition of growth.

Example 7

Modes of antibacterial action of NK-lysin peptides were characterized with the following assays.
Leakage of Intracellular Contents Inhibition of bacterial growth was thought to be due to membrane damage that occurs when the cultures are treated with NK-lysin peptides. To confirm membrane damage, Nanodrop was used to quantify the release of nucleic acids from *S. typhimurium* after treatment with NK lysin peptide. The release of nucleic acids from *S. typhimurium* after membrane damage due to exposure to NK lysin peptide can be detected by reading changes in OD at 260 nm over time. After incubation periods of 15, 30 and 90 mins, OD 260 nm readings were taken. The chicken NK lysin peptide showed a higher activity (greater release of DNA/RNA) compared to the bovine and human NK-lysin peptides at 15 min, but there were no significant differences between the three peptides at 30 min and 90 min, respectively. When NK lysin peptide isolated from humans were used the action of the peptide against *S. typhi* showed increased action at 15 min, compared to increase in action of chicken NK lysin at 30 and 90 min of exposure. These results were confirmed by gel electrophoresis and quantification a 500 bp fragment of 16s rRNA amplified using PCR. Amplified fragments were visualized with ethidium bromide staining and compared with markers of specific DNA ladder (data not shown).

Bacteriolytic Potential

Figure 11A:
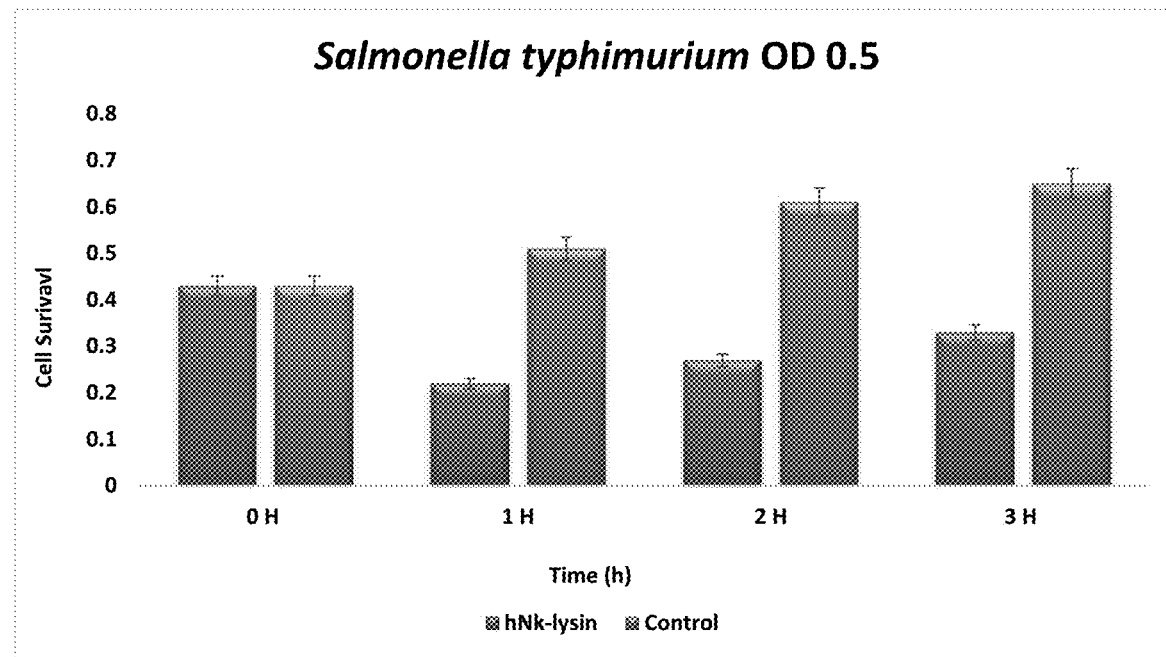
FIGS. 11A and 11B show the bacterial lytic effect of 1×MIC human NK-lysin peptide against *Salmonella typhimurium* (ATCC 14028) at two different inoculum concentrations. Data presented as means (±SD) of three independent repeats in triplicate.
Figure 11B:
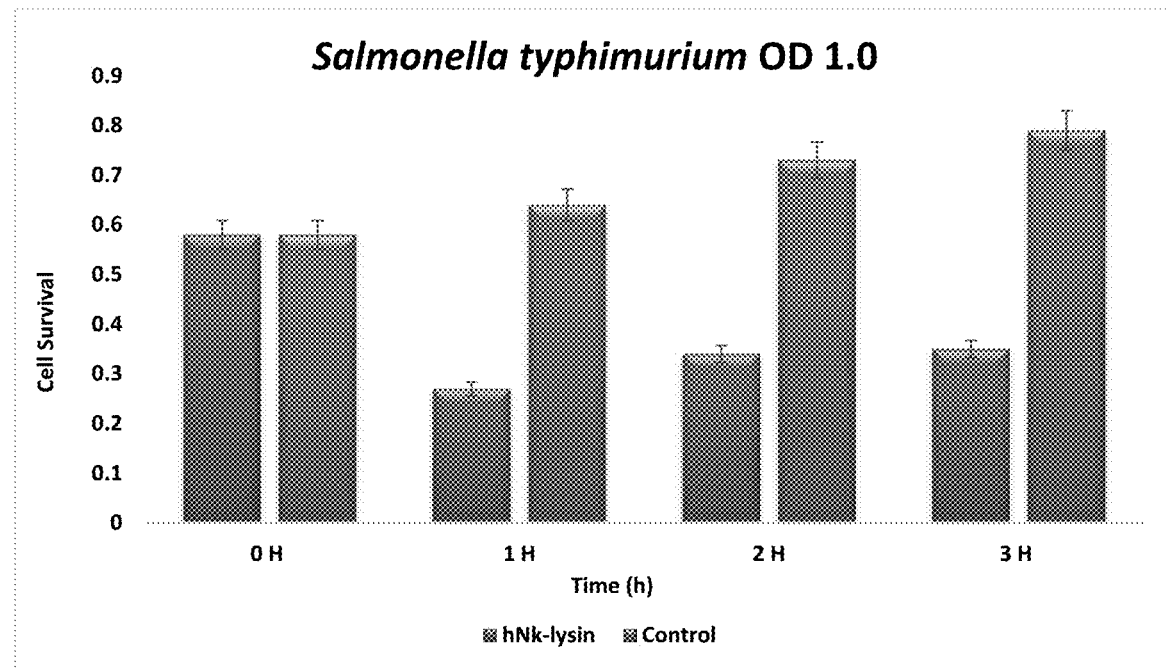
Figure 12A:
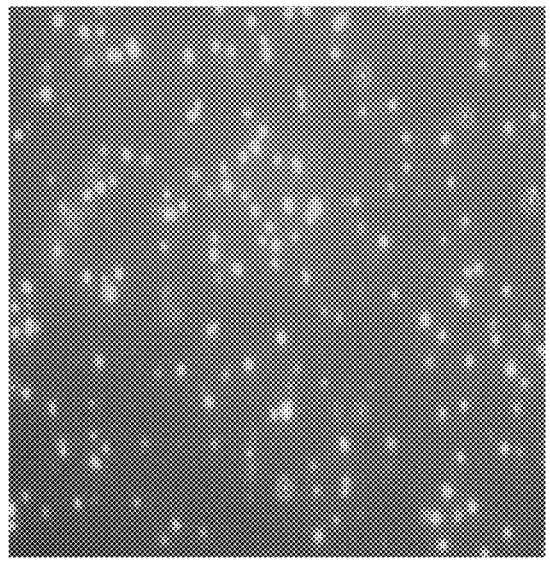
FIGS. 12A-12D demonstrate the membrane damage to *Salmonella typhimurium* (ATCC 14028) following treatment with NK-lysin peptides.
Figure 12B:
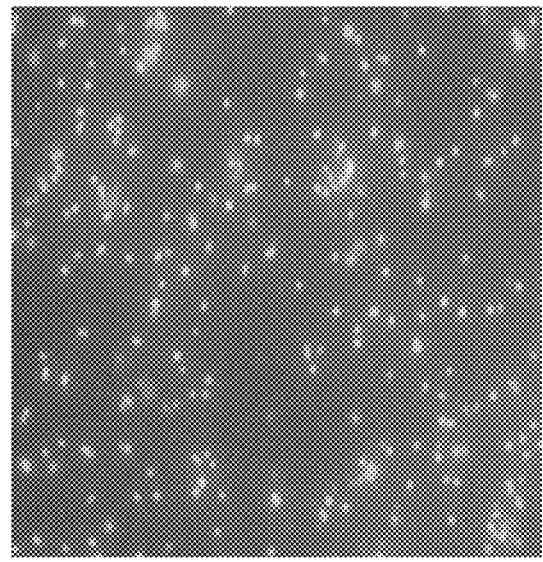
Figure 12C:
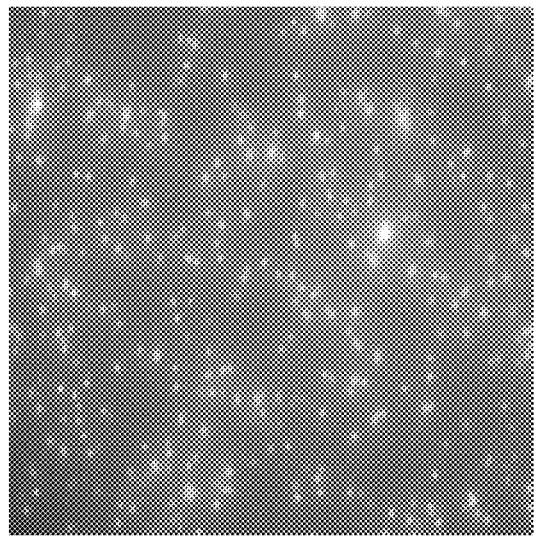
Figure 12D:
Figure 13:
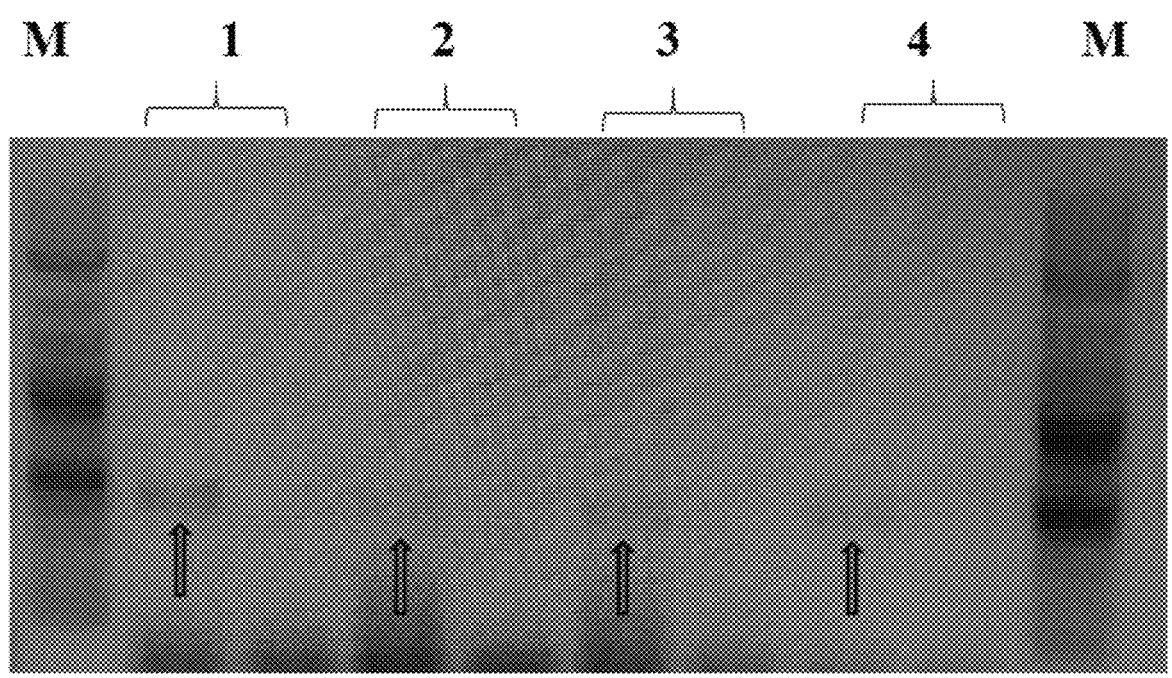
FIG. 13 shows the results of PCR-amplification of a 499 bp fragment of the CTX-M1 gene from samples of untreated and NK-lysin-treated bacterial cultures. Arrows indicate gene amplicon from untreated bacteria, whereas next lane indicates absence of amplicon from NK-lysin-treated bacteria. The bracketed pairs of lanes contain PCR-amplified samples from untreated and treated bacteria as follows: 1) *Salmonella typhimurium* ATCC 14028; 2) *P. aeruginosa* (ATCC 9027); 3) *Klebsiella oxytoca* (ATCC 49131); 4) *S. pyrogens* (ATCC 19615). Lanes M contain DNA ladder size markers.

This experiment poses the question as to whether these peptides would work at higher concentration of bacterial strains or not and compares the effect of bovine and human against two concentrations of *Salmonella typhimurium* at concentrations of (0.5) OD600 and (0.1) OD600). Bacteriolytic potential of bovine and human NK-lysin peptides were tested using two different inoculums of bacteria which were the OD600 (0.5) and OD600 (1.0) were used for screening. The bacterial inoculum of *Salmonella typhimurium* with concentration OD600 (0.5) incubated for 1 hr with bovine NK-lysin peptide had a survival rate that fell to approximately half of the starting culture, while the survival/growth of the control culture continued to survive and grow. After 2 hr of incubation bacteria survival was less than half of that measured for control. This trend continued even after 3 hr with onset of minor modification in growth of cell as depicted in FIG. 6 for bovine NK-lysin peptides as seen in FIG. 11.

The bacterial survivability in the presence of human NK-lysin peptides measured at OD600 (1.0) was 27%, 34% and 35% after 1, 2 and 3 hours, respectively, passed. A similar trend was observed for bovine NK-lysin peptide, which is shown in FIG. 7, there is very little deviation. By incubating with 1×MIC of peptide the lysis of cell was 79%, 72% and 68% shown after 1, 2 and 3 hours have passed on the concentration of OD600 (0.5). Similar to human NK lysin peptide, at OD 600 (1.0) there was significant decrease in growth by 74, 76 and 64% after 1, 2 and 3 hours passed respectively. The lysis activity of both bovine and human NK lysin peptides at their respective MICs was similar as shown in FIG. 12.

Membrane Damage with NK-Lysin Peptides

Figure 14:
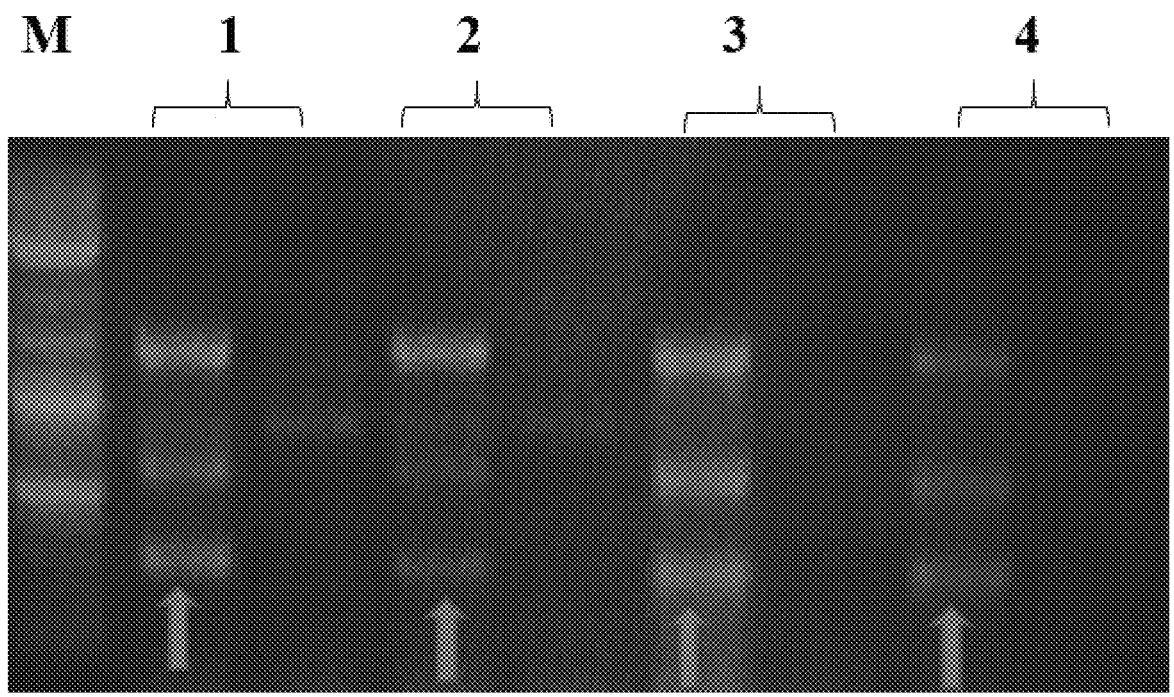
FIG. 14 shows pairs of a PCR-amplified 307 bp fragment of CTX-M8 gene from samples of untreated and NK-lysin-treated bacterial cultures. Arrows indicate gene amplicon from untreated bacteria, whereas next lane indicates absence of amplicon from NK-lysin-treated bacteria. The bracketed pairs of lanes contain PCR-amplified samples from untreated and treated bacteria as follows: 1) *Salmonella typhimurium* (ATCC 14028); 2) *Pseudomonas aeruginosa* (ATCC 9027); 3) *Klebsiella oxytoca* (ATCC 49131); 4) *Streptococcus pyrogens* (ATCC 19615). Lane M contains DNA ladder size markers.

To evaluate whether NK lysin peptides alter morphology and survivability of *S. typhimurium*, a fluorescent stain, 4′,6-diamidino-2-phenylindole (DAPI), which stains dead cells but is restricted from entering live cells with intact membranes. After staining with DAPI, fluorescent microscopy was used to assess whether any damage was done to *S. typhimurium* cell membranes after being treated with NK lysin peptides. The results showed that a majority of untreated *S. typhimurium* plasma membranes remained intact, but treatment with 2×MIC of NK-lysin peptides induced damage to most of the *S. typhimurium*, which were more permeable to the stain and thus brightly stained. FIG. 14 shows representative images of the damage done by chicken, bovine and human NK-lysin peptides, while the untreated control bacteria were able to exclude the DAPI and remained unstained.

Example 8

Detection of β-Lactam-Resistance and Quinolon-Resistance Genes

The treatments with NK-lysin peptide provided evidence of the presence/absence of plasmid-mediated quinolone-resistance and β-lactam-resistance genes for all gram negative and positive bacteria studies, as shown in Table 3. A summary of the results is shown in Table 4.

TABLE 4

Detection of quinolone-resistance and β-lactam-resistance genes untreated and NK-lysin treated bacteria.

| Gene name | Untreated | Treated |
|---|---|---|
| $^{bla}$TEM-1 | + | + |
| Toho-1 | − | − |
| CTX-M1 | + | − |
| CTX-M-8 | + | − |
| CTX-M-9 | + | − |
| Gyrase A | + | − |
| QnrA | − | − |
| QnrB | − | − |
| QnrD | − | − |
| QnrS | − | − |

Figure 15:
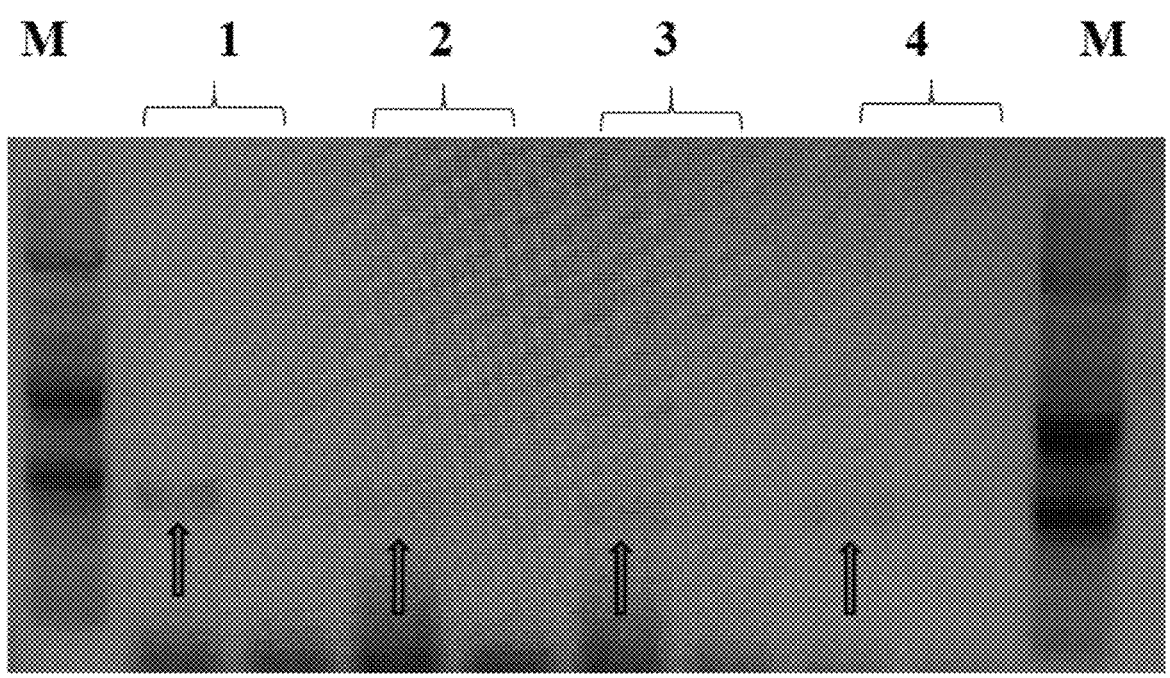
Figure 16:
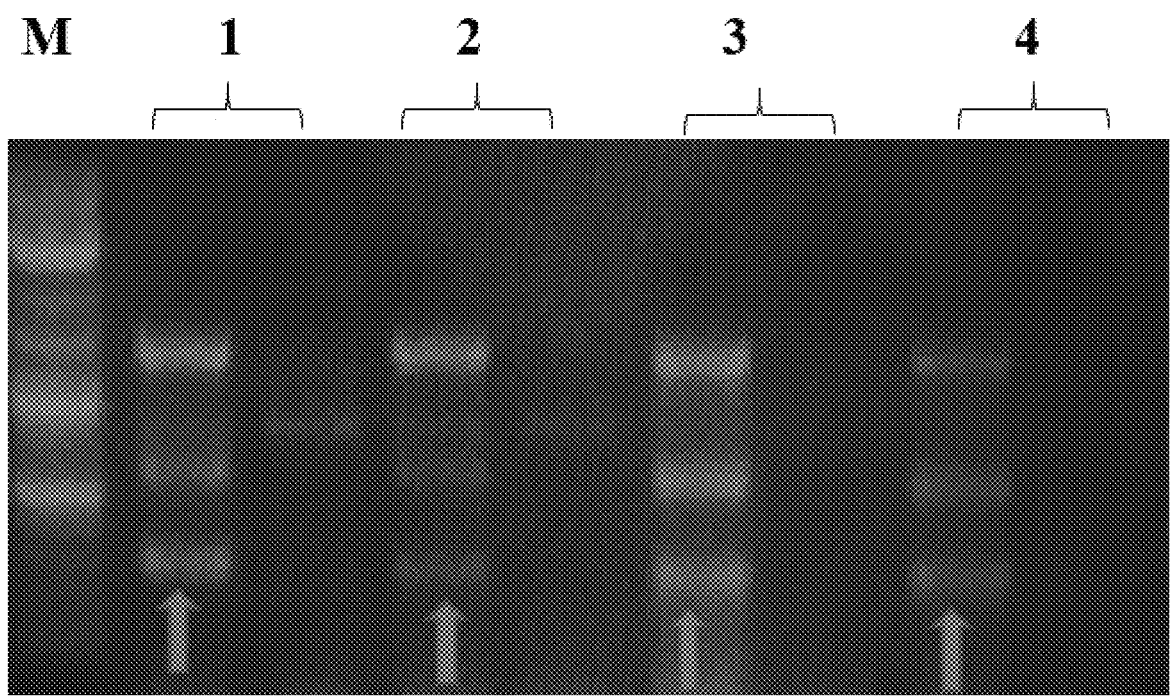

The dominant β-lactamase gene known as $^{bla}$TEM-1 was present in both treated and untreated bacteria, whereas Toho-1 was not found in untreated or treated bacteria. While β-lactamase genes CTX-M-1, CTX-M-8, and CTX-M-9 were detected in untreated bacteria, none of these were found in any of the bacterial stains after treatment with NK-lysin peptide, as shown in Table 4 and FIGS. 15 and 16. The presence of gyrase A, a chromosomal gene associated with topoisomerase 2, was detected in untreated and treated bacteria. In contrast, the QnrA, QnrB, QnrD, and QnrS genes associated with plasmid-mediated quinolone-resistance were not detected in any bacteria, irrespective of whether untreated or treated. These data indicate that NK-lysin peptide treatment effectively inhibited β-lactamase genes $^{bla}$TEM-1, CTX-M-1, CTX-M-8, and CTX-M-9 were inhibited or suppressed and may be used in combination with one or more (3-lactam antibiotics to treat an infection caused by β-lactam-resistant bacteria.

Example 9

Cytotoxicity and Antiviral Activity of NK-Lysin Peptides

Rotavirus (strain SA-11) was used to evaluate the antiviral action of the three NK-lysin peptides in a mammalian cell type in vitro. MA-104 cells were first tested to confirm that the peptides alone were safe and nontoxic. Cytotoxity of the NK lysin peptides at a concentration of 80 μg/ml was then tested against rotavirus infection of MA-104 cells. Each species of the NK-lysin peptides was combined with an equal volume of the rotavirus stock solution described above and incubated for 1 hr at 37° C. Microplates with MA-104 cells plated at equal density were preincubated and then treated with an array of rotavirus/peptides mixtures except for wells that were untreated control MA-104 cells. The microplates were incubated for 5 days at 37° C. under 5% $CO_2$. Data is summarized in Table 5 showing various levels of antiviral activity against the rotavirus. The bovine NK-lysin peptides showed the highest degree of antiviral activity, with 90% inhibition of infection. Chicken NK-lysin peptide showed similar results with 80% inhibition, whereas inhibition with human NK-lysin peptide was the lowest at 50% inhibition.

TABLE 5

The antiviral activity of chicken, bovine or human NK-lysin peptides at a concentration of 80 μg/ml against Rotavirus (SA-11).

| Peptides | TCID50/ml | $Log_{10}$TCID50/ml | Log reduction | % reduction |
|---|---|---|---|---|
| Initial titre | $1.95 \times 10^6$ | 6.29 | NA | NA |
| cNK-lysin | $4.11 \times 10^5$ | 5.61 | 0.7 | 79% |

TABLE 5-continued

The antiviral activity of chicken, bovine or human NK-lysin peptides at a concentration of 80 μg/ml against Rotavirus (SA-11).

| Peptides | TCID50/ml | $Log_{10}$TCID50/ml | Log reduction | % reduction |
|---|---|---|---|---|
| bNK-lysin | $1.95 \times 10^5$ | 5.29 | 1.00 | 90% |
| hNK-lysin | $1.00 \times 10^6$ | 6.00 | 0.29 | 49% |

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

We claim:

1. A method of treating a bacterial infection wherein the bacterial infection is caused by a pathogen that is or is suspected to be resistant to β-lactam antibiotics, comprising the step of co-administering at least one β-lactam antibiotic and a therapeutically effective amount of NK-lysin peptide, wherein the therapeutically effective amount of NK-lysin peptide is sufficient to inhibit expression of at least one bacterial β-lactamase gene selected from the group consisting of CTX-M-1, CTX-M-8 and CTX-M-9, wherein the NK-lysin peptide has an amino acid sequence selected from the group consisting of SEQ ID NO. 1, SEQ ID NO. 2, and SEQ ID NO. 3.

* * * * *